US006516211B1

(12) United States Patent
Acker et al.

(10) Patent No.: US 6,516,211 B1
(45) Date of Patent: Feb. 4, 2003

(54) MRI-GUIDED THERAPEUTIC UNIT AND METHODS

(75) Inventors: David E. Acker, Setauket; Mark Wagshul, Patchogue, both of NY (US)

(73) Assignee: Transurgical, Inc., Setauket, NY (US)

( * ) Notice: Subject to any disclaimer, the term of this patent is extended or adjusted under 35 U.S.C. 154(b) by 0 days.

(21) Appl. No.: 09/610,826

(22) Filed: Jul. 6, 2000

Related U.S. Application Data

(62) Division of application No. 09/083,414, filed on May 22, 1998.
(60) Provisional application No. 60/047,526, filed on May 23, 1997, provisional application No. 60/054,124, filed on Jul. 28, 1997, provisional application No. 60/062,518, filed on Oct. 17, 1997, provisional application No. 60/074,474, filed on Feb. 12, 1998, and provisional application No. 60/075,324, filed on Feb. 20, 1998.

(51) Int. Cl.[7] .............................................. A61B 5/055
(52) U.S. Cl. ................................... 600/411; 601/3
(58) Field of Search ................................. 600/410, 411, 600/439; 601/3, 2, 4; 324/307, 309, 318

(56) References Cited

U.S. PATENT DOCUMENTS

| 4,341,222 A | 7/1982 | Gardineer et al. |
| 4,406,059 A | 9/1983 | Scott et al. ..................... 29/857 |
| 4,543,959 A | 10/1985 | Sepponen .................... 128/653 |
| 4,554,925 A | 11/1985 | Young ........................ 128/653 |

(List continued on next page.)

FOREIGN PATENT DOCUMENTS

| EP | 0 627 206 A2 | 12/1994 |
| EP | 0 654 675 A1 | 5/1995 |
| WO | WO 96/33666 | 10/1996 |

OTHER PUBLICATIONS

"Optimization of Spoiled Gradient–Echo Phase Imaging for in Vivo Localization of a Focused Ultrasound Beam", Chung, et al., MRM, 1996, vol. 36, pp. 745–752.

"Simultaneous Magnetic Resonance Phase and Magnitude Temperature Maps in Muscle", Cline, et al., MRM 1996, vol. 35, pp. 309–315.
"Focused US System for MRI–Imaging–guided Tumor Ablation"., Cline, et al., Radiology, 1995, vol. 194, pp. 731–737.
MR Monitoring of Focused Ultrasonic Surgery of Renal Cortex: Experimental and Simulation Studies. Hynynen, et al., JMRI, 1995, vol. 5, pp. 259–266.
MR Temperature Mapping of Focused Ultrasound Surgery, Cline, et al., MRM, 1994, vol. 31, pp. 628–636.
"Interventional Use of Magnetic Resonance Imaging", Jolesz, et al., Magnetic Resonance Quarterly, vol. 10, No. 2, pp. 85–96, 1994.
"Multiple–Focus ultrasound Phased–Array Pattern Synthesis: Optimal Driving–Signal Distributions for Hyperthermia", Ebbini, et al., Transactions IEEE, 1989, pp. 540–548.
"Control of the Necrosed Tissue Volume During Noninvasive Ultrasound Surgery Using a 16–Element Phased Array", Fan, et al., Medical Physics, vol. 22, Mar. 1995, pp. 297–306.

*Primary Examiner*—Marvin M. Lateef
*Assistant Examiner*—Eleni Mantis Mercader
(74) *Attorney, Agent, or Firm*—Lerner, David, Littenberg, Krumholz & Mentlik, LLP

(57) ABSTRACT

Magnetic resonance information acquired by a movable magnetic resonance instrument is used to monitor hyperthermia treatments such as tissue ablation. The instrument may include both the magnetic resonance equipment and an energy applicator such as a high intensity focused ultrasound unit. The treatment can be conducted under automatic control after the operator marks a treatment volume on an image of the subject, such as a magnetic resonance image acquired using the movable magnetic resonance instrument. The automatic treatment can be based on interpolation of tissue response curves at plural test points near the treatment volume. The system can also provide automatic supervisory control during manual operation, to prevent application of heat to sensitive anatomical structures.

15 Claims, 9 Drawing Sheets

U.S. PATENT DOCUMENTS

| | | | | |
|---|---|---|---|---|
| 4,587,504 | A | 5/1986 | Brown et al. | 335/216 |
| 4,620,546 | A | 11/1986 | Aida et al. | 128/660 |
| 4,638,436 | A | 1/1987 | Badger et al. | 607/102 |
| 4,701,736 | A | 10/1987 | McDouglall et al. | 335/299 |
| 4,721,914 | A | 1/1988 | Fukushima et al. | 324/320 |
| 4,748,412 | A | 5/1988 | Yamamoto et al. | |
| 4,787,888 | A | 11/1988 | Fox | |
| 4,875,485 | A | 10/1989 | Matsutani | 128/653 |
| 4,893,624 | A | 1/1990 | Lele | 601/3 |
| 4,914,608 | A | 4/1990 | LeBihan et al. | 364/557 |
| 4,936,303 | A | 6/1990 | Detwiler et al. | 601/3 |
| 4,938,216 | A | 7/1990 | Lele | 601/3 |
| 4,951,688 | A | 8/1990 | Keren | 128/804 |
| RE33,590 | E | 5/1991 | Dory | 128/660.03 |
| 5,023,554 | A | 6/1991 | Cho et al. | 324/309 |
| 5,042,487 | A | 8/1991 | Marquardt | 128/653 |
| 5,054,470 | A | 10/1991 | Fry et al. | 601/2 |
| 5,080,101 | A | 1/1992 | Dory | 128/660.03 |
| 5,146,924 | A | 9/1992 | Sepponen | 128/653.2 |
| 5,150,710 | A | 9/1992 | Hall et al. | 128/653 |
| 5,153,546 | A | 10/1992 | Laskaris | 335/216 |
| 5,178,148 | A | 1/1993 | Lacoste et al. | 128/660.03 |
| 5,189,687 | A | 2/1993 | Bova et al. | |
| 5,207,222 | A | 5/1993 | Koizumi et al. | 128/653.2 |
| 5,247,935 | A | 9/1993 | Cline et al. | 128/653 |
| 5,284,144 | A | 2/1994 | Delannoy et al. | 128/653.2 |
| 5,291,890 | A | 3/1994 | Cline | 600/411 |
| 5,304,930 | A | 4/1994 | Crowley et al. | 324/309 |
| 5,307,812 | A | 5/1994 | Hardy et al. | 128/653.2 |
| 5,323,779 | A | 6/1994 | Hardy et al. | 128/653.2 |
| 5,327,884 | A | 7/1994 | Hardy et al. | 128/653.2 |
| 5,354,258 | A | * 10/1994 | Dory | 601/3 |
| 5,368,032 | A | 11/1994 | Cline et al. | 128/653.2 |
| 5,431,621 | A | 7/1995 | Dory | 601/2 |
| 5,436,607 | A | 7/1995 | Chari et al. | 335/216 |
| 5,443,068 | A | 8/1995 | Cline et al. | 128/653.5 |
| 5,474,072 | A | 12/1995 | Shmulewitz | |
| 5,485,839 | A | 1/1996 | Aida et al. | 128/653.1 |
| 5,492,122 | A | 2/1996 | Button et al. | 128/653.2 |
| 5,523,058 | A | 6/1996 | Umemura et al. | |
| 5,549,638 | A | 8/1996 | Burdette | 601/3 |
| 5,553,618 | A | 9/1996 | Suzuki et al. | 128/653.2 |
| 5,558,091 | A | 9/1996 | Acker et al. | 128/653.1 |
| 5,590,653 | A | 1/1997 | Aida et al. | 128/653.2 |
| 5,601,526 | A | 2/1997 | Chapelon et al. | |
| 5,627,471 | A | 5/1997 | Kinamen | |
| 5,643,179 | A | 7/1997 | Fujimoto | |
| 5,665,054 | A | 9/1997 | Dory | 601/3 |
| 5,666,954 | A | 9/1997 | Chapelon et al. | 128/660.03 |
| 5,694,936 | A | 12/1997 | Fujimoto et al. | |
| 5,720,287 | A | 2/1998 | Chapelon et al. | 128/660.03 |
| 5,743,862 | A | 4/1998 | Izumi | |
| 5,759,162 | A | 6/1998 | Oppelt et al. | 601/2 |
| 5,859,891 | A | 1/1999 | Hibbard | |
| 5,895,356 | A | 4/1999 | Andrus et al. | 600/439 |
| 5,900,793 | A | 5/1999 | Katznelson et al. | |
| 5,938,600 | A | 8/1999 | Van Vaals et al. | 600/411 |
| 6,029,081 | A | 2/2000 | DeMeester et al. | |
| 6,088,613 | A | 7/2000 | Unger | |
| 6,112,112 | A | 8/2000 | Gihuijs et al. | |
| 6,126,619 | A | 10/2000 | Peterson et al. | |
| 6,208,142 | B1 | 3/2001 | Wagshul | |

\* cited by examiner

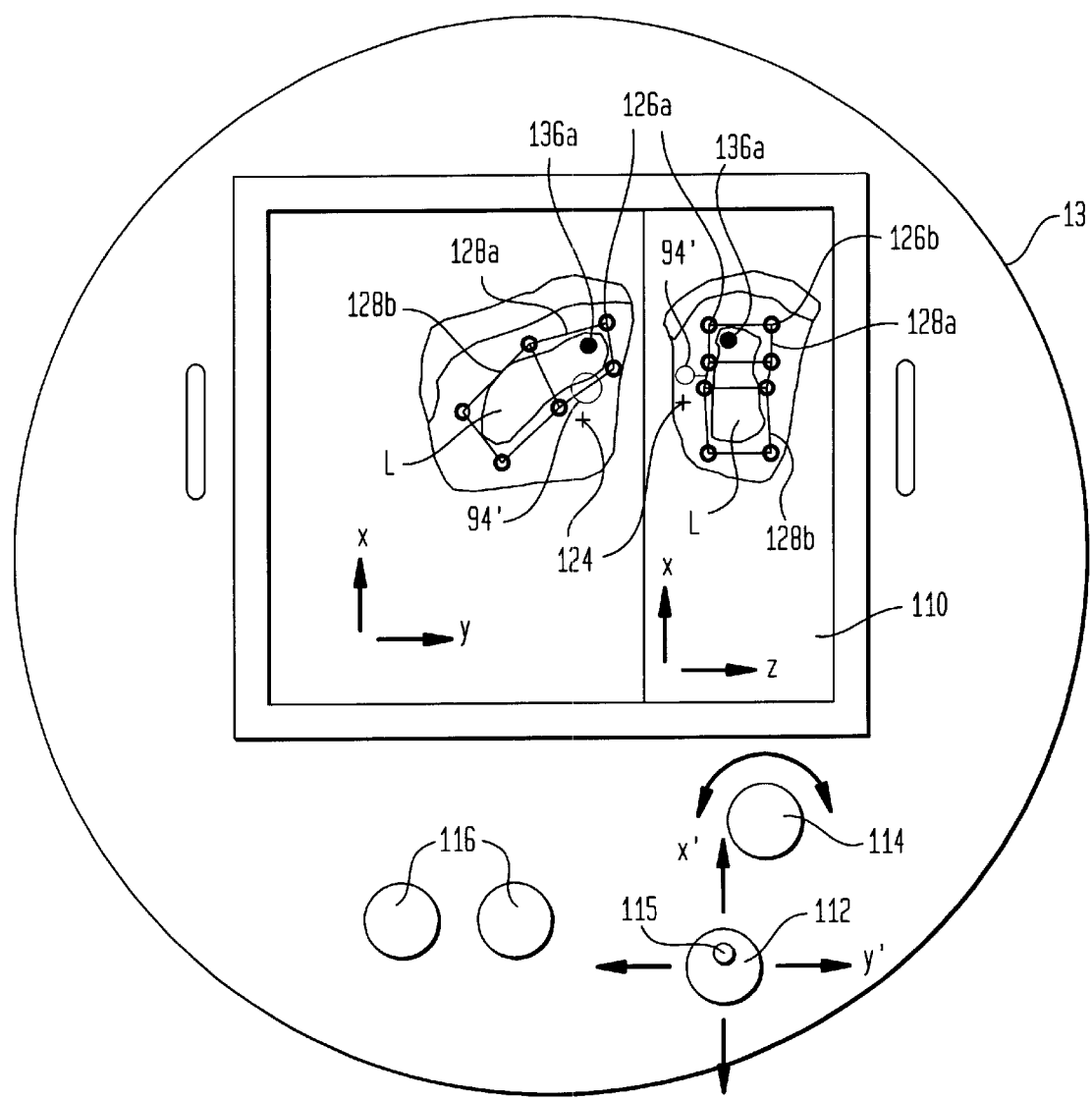

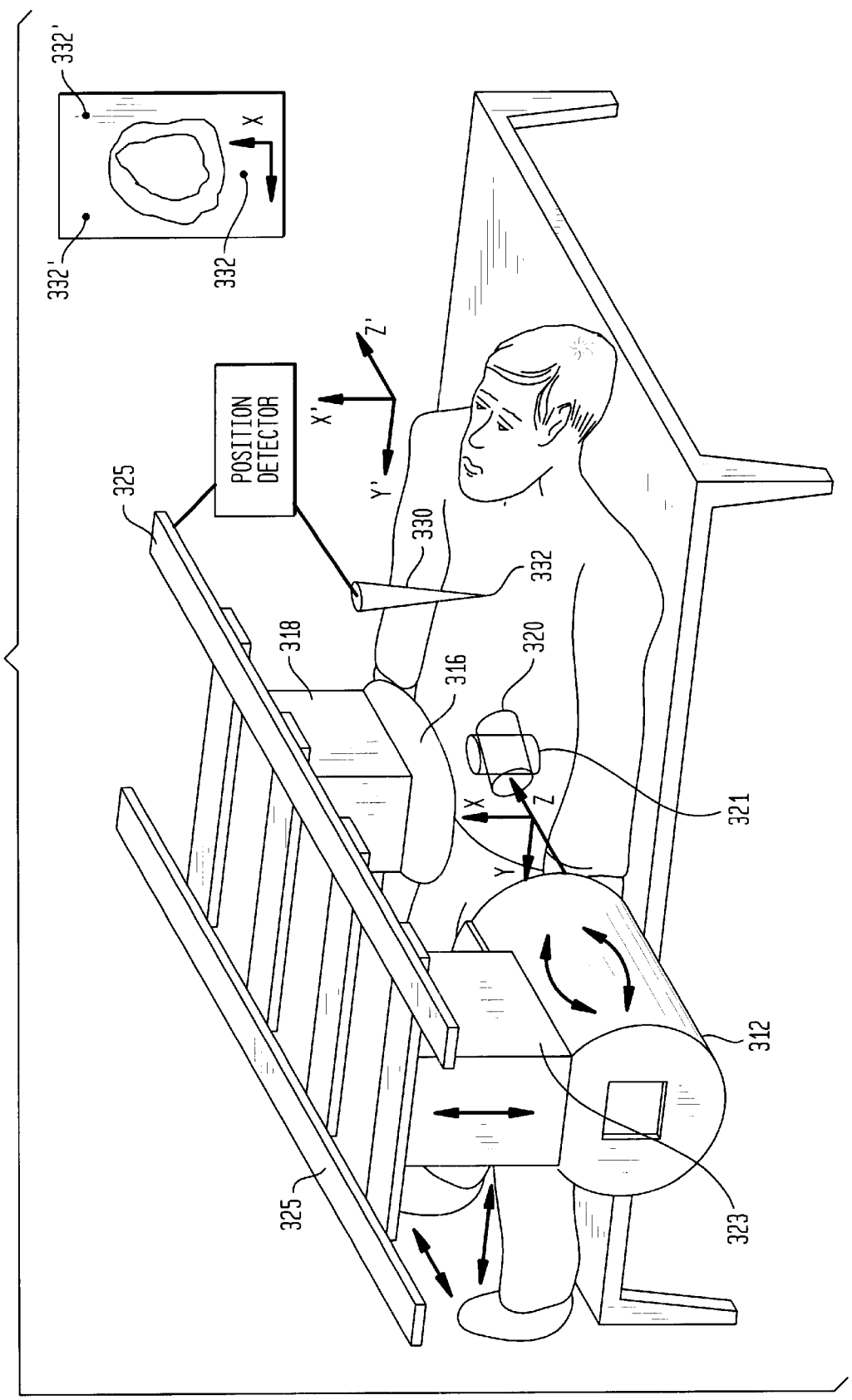

MRI-GUIDED THERAPEUTIC UNIT AND METHODS

CROSS-REFERENCE TO RELATED APPLICATION

The present application is a divisional of U.S. patent application 09/083,414 filed May 22, 1998 which claims benefit of United States Provisional Patent Applications No. 60/047,526, filed May 23, 1997; No. 60/054,124, filed Jul. 28, 1997; No. 60/062,518, filed Oct. 17, 1997; No. 60/074,474, filed Feb. 12, 1998; and No. 60/075,324, filed Feb. 20, 1998. The disclosures of all of the aforesaid applications are incorporated herein by reference.

FIELD OF THE INVENTION

The present invention relates to the art of intrabody therapy involving application energy to the body and further relates to monitoring of such therapy by magnetic resonance.

BACKGROUND OF THE INVENTION

Various forms of therapy can be applied within the body of a human or other mammalian subject by applying energy from outside of the subject. In hyperthermia, ultrasonic or radio frequency energy is applied from outside of the subject's body to heat the tissues. The applied energy can be focused to a small spot within the body so as to heat the tissues at such spot to a temperature sufficient to create a desired therepeautic effect. This technique can be used to selectively destroy unwanted tissue within the body. For example, tumors or other unwanted tissues can be destroyed by applying heat to heat the tissue to a temperature sufficient to kill the tissue, commonly to about 60° to 80° C., without destroying adjacent normal tissues. Such a process is commonly referred to as "thermal ablation". Other hyperthermia treatments include selectively heating tissues so as to selectively activate a drug or promote some other physiologic change in a selected portion of the subject's body. Other therapies use the applied energy to destroy foreign objects or deposits within the body as, for example, in ultrasonic lithotripsy.

Magnetic resonance is used in medical imaging for diagnostic purposes. In magnetic resonance imaging procedures, the region of the subject to be imaged is subjected to a strong magnetic field. Radio frequency signals are applied to the tissues of the subject within the imaging volume. Under these conditions, atomic nuclei are excited by the applied radio frequency signals and emit faint radio frequency signals, referred to herein as magnetic resonance signals. By applying appropriate gradients in the magnetic field during the procedure, the magnetic resonance signals can be obtained selectively from a limited region such as a two-dimensional slice of the subject's tissue. The frequency and phase of the signals from different portions of the slice can be made to vary with position in the slice. Using known techniques, it is possible to deconvolute the signals arising from different portions of the slice and to deduce certain properties of the tissues at each point within the slice from the signals.

Various proposals have been advanced for using magnetic resonance to monitor and guide application of energy within the body. As disclosed, for example, in the U.S. Pat. Nos. 4,554,925, 4,620,546 4,951,688 and 5,247,935, the disclosures of which are hereby incorporated by reference herein, certain known magnetic resonance procedures are temperature sensitive, so that magnetic resonance data acquired using these procedures will indicate changes in temperature of the tissues. For example, a magnetic resonance parameter referred to as $T_1$ or spin-lattice relaxation time will vary with temperature. If magnetic resonance imaging apparatus is actuated to acquire $T_1$ for various volume elements or "voxels" within the subject, the data for different voxels will vary with temperature, at least within a tissue having generally the same composition. The data can be portrayed as a visible image and hence different temperatures can be shown by the differences in brightness or color within the displayed image. Thus, the location within the body being heated can be monitored by monitoring such a visible image during application of energy to the body. Also, the degree of the heating can be monitored by monitoring $T_1$ for the heated regions. Magnetic resonance parameters other than $T_1$ can be portrayed or monitored in the same way.

Although these procedures have well been known, they have not been widely adopted in the medical community. Magnetic resonance imaging instruments of the types commonly used for medical diagnostic applications include large, precise magnets which are arranged to impose a high magnetic field, typically about one Tesla or more over a relatively large imaging volume typically 10 cm or more in diameter. Certain magnetic resonance imaging static field magnets severely limit access to the subject. For example, a solenoidal air-core superconducting magnet may have superconductive coils surrounding a tubular subject-receiving space. The subject lies on a bed which is advanced into the said tubular space so that the portion of the patient to be imaged is disposed inside of the tubular space. Iron core magnets typically have ferromagnetic frames defining opposed poles and a subject-receiving space lying between the poles. Permanent magnets or electromagnets are associated with the frame for providing the required magnetic flux. Depending upon the design of the magnet, either the superconductive coils or the frame may obstruct access to the patient during operation of the magnetic resonance instrument. Moreover, because the magnetic resonance imaging instruments typically employed in medicine are expensive, fixed structures, there are substantial costs associated with occupancy of the instrument. Because hyperthermia procedures typically require significant time to perform, it is expensive to perform these procedures while the patient is occupying the magnetic resonance imaging instrument. Moreover, because instruments of this type are typically found only in specialized imaging centers and radiology departments of hospitals, use of the magnetic resonance imaging instrument for therapeutic procedures is associated with considerable inconvenience to the patient and to the treating physician. Thus, despite all of the efforts devoted heretofore to MRI-guided hyperthermia procedures and apparatus, there remains a considerable, unmet need for improvements in such procedures and apparatus which would reduce the cost and increase the convenience of such procedures.

Moreover, there has been a need for further improvement in hyperthermia procedures of this type. The physician typically aims the energy-applying device manually and applies so-called "subthreshold" doses of energy, sufficient to heat the tissues slightly but insufficient to cause permanent change in the tissue. The physician then observes the location of the heated spot on a magnetic resonance image to confirm that the energy-applying device is aimed at the desired location in the subject's body.

The response of the tissues within the body to the applied energy varies. Differences in tissue properties such as specific heat and thermal conductivity will cause differences in the change in the temperature caused by absorption of a specific amount of energy. The "susceptibility" or tendency of the tissues to absorb the applied energy also varies from place to place. Therefore, after the device has been aimed onto a particular spot, the physician must apply a therapeutic dose by gradually increasing the amount of the energy applied to the spot and monitoring the degree of temperature change to the spot by means of the magnetic resonance information as, for example, by observing the visually displayed magnetic resonance image.

Typically, the spot heated during each operation of the energy-applying device is relatively small as, for example, a spot about 1 mm–3 mm in diameter. To treat a large region within the subject, the spot must be repositioned many times. All of this requires considerable time and effort. Moreover, the procedure is subject to errors which can cause damage to adjacent organs. For example, thermal energy is commonly applied to treat benign prostatic hyperplasia or tumors of the prostate gland. If the physician mistakenly aims the energy-applying device at the urethra and actuates it to apply a therapeutic dose, the delicate structure of the urethra can be destroyed. Therefore, improvements in thermal energy treatments which improve the safety of such treatments and reduce the effort required to perform such treatments, would be desirable.

SUMMARY OF THE INVENTION

The present invention addresses these needs.

One aspect of the present invention provides therapeutic apparatus. Apparatus according to this aspect of the invention desirably includes a movable static field magnet adapted to apply a static magnetic field in a magnetic resonance volume at a predetermined disposition relative to the static field magnet and also includes an energy applicator adapted to apply energy within an energy application zone at a predetermined disposition relative to the applicator. Apparatus according to this aspect of the invention also includes positioning means for moving the static field magnet and the energy applicator to position the magnet and the applicator so that the magnetic resonance volume at least partially encompasses a region of the subject to be treated and so that the energy application zone associated with the applicator intersects the magnetic resonance volume within the region of the subject to be treated. Preferably, the apparatus includes a chassis and both the static field magnet and the energy applicator are mounted to the chassis. The positioning means in this case includes means for moving the chassis so as to position the chassis relative to the subject. The static field magnet desirably is a single-sided static field magnet arranged so that the magnetic resonance volume is disposed outside of the static field magnet and spaced from the static field magnet in a forward direction. The static field magnet most preferably is substantially smaller than the static field magnets utilized in conventional magnetic resonance imaging instruments. For example, the static field magnet may have dimensions of a meter or less and may be light enough to be moved readily by a positioning device of reasonable cost and proportions. Thus, the entire apparatus can be moved as required to position it adjacent to the region of the subject's body which requires treatment. The most preferred apparatus according to this aspect of the present invention is small enough and inexpensive enough to be used in a clinical setting such as a physician's office or medical center. Thus, it is feasible to perform magnetic resonance-monitored energy applying procedures in a normal clinical setting. There is no need to occupy an expensive diagnostic magnetic resonance imaging instrument during such procedures.

Additional aspects of the present invention provide improved single-sided static-field magnets for magnetic resonance. Even with such improvements, however, the small single-sided static field magnet typically is capable of providing a magnetic field suitable for magnetic resonance imaging only in a relatively small magnetic resonance volume as, for example, a magnetic resonance volume with dimensions of a few centimeters. Such a small imaging volume normally would be regarded as undesirable in an instrument for general purpose magnetic resonance imaging purposes. However, instruments according to this aspect of the present invention incorporate the realization that energy-applying procedures are applied within relatively small regions of the subject's anatomy, so that an instrument with a small magnetic resonance volume still can provide useful information for controlling the energy-applying procedures. Moreover, the image quality which is required for control of energy application is less than that which is required in diagnostic MRI imaging. The use of a relatively small magnetic resonance volume then permits use of a single-sided magnet which is relatively small, light weight and inexpensive.

Apparatus according to this aspect of the invention desirably also includes ancillary equipment such as gradient coils for applying a magnetic field gradient within the magnetic resonance volume. The gradient coils may be mounted to the chassis or otherwise secured in position relative to the static field magnet. The apparatus may also include radio frequency equipment for applying radio frequency signals to the subject and receiving the resulting magnetic resonance signals, as well as devices for actuating the gradient coils to apply the field gradients. The apparatus may further include a computer for processing the magnetic resonance signals such as to derive an image of tissues of the subject within the magnetic resonance volume in working frame of reference such as the local magnetic resonance frame of reference, the frame of reference of the static field magnet. The computer can also process the magnetic resonance signals to derive temperatures of tissues of the subject at one or more locations in the working frame of reference.

The energy applicator may include an array of ultrasound-emitting transducers and may also include a flexible fluid container mounted between the ultrasound transducer array and the energy application zone so that the flexible fluid container can be engaged between the transducer array and a surface of the subject's body. In a particularly preferred arrangement, the energy applicator includes a mounting and the array of transducers and the flexible fluid container are provided as a disposable unit releasably coupled to the mounting. Stated another way, the permanent component of the apparatus may include, as the energy applying device, a mounting suitable for receiving such a disposable unit. Typically, the mounting provides electrical connections for the transducer array and also provides mechanical securement for the disposable unit. In a particularly preferred arrangement, the apparatus includes a radio frequency antenna in the form of a loop for transmitting or receiving RF signals. The antenna is secured in position to the mounting so that when the ultrasonic transducers array and flexible fluid container are secured to the mounting, the antenna encircles the flexible fluid container at or near the surface of the patient's body. The static field magnet is typically arranged to provide a magnetic field directed in an axial direction, along a central axis. Desirably, the energy applicator and RF antenna are positioned so that an applicator axis extending from the applicator into the overlapping portions of the energy application volume and magnetic resonance volume is transverse to the central axis of the static field magnet. The RF loop antenna axis is also transverse to the central axis of the static field magnets. As further discussed below, this arrangement is convenient to use and also enhances the interaction between the transmitted RF signals and the atomic nuclei in the imaging volume as well as the signal to noise ratio of the received magnetic resonance signals.

A further aspect of the invention provides magnetic resonance apparatus, in particular, imaging apparatus incorporating movable single-sided static field magnets and positioning devices as discussed above. Magnetic resonance apparatus according to this aspect of the invention may serve as a component of the treatment apparatus as may also be used independently to provide images of regions in the subject for other purposes.

A further aspect of the present invention provides methods of treating living subjects, such as a human or other mammalian subject. Methods according to this aspect of the invention include the steps of positioning a movable static field magnet adapted to apply a static field in a magnetic resonance volume, the magnet being positioned relative to the subject so that the magnetic resonance volume at least partially encompasses a region of the subject to be treated. A movable applicator adapted to apply energy within an energy application zone is positioned relative to the subject so that the energy application zone intersects the magnetic resonance volume within the region of the subject requiring treatment. While the static field magnet is applying the static magnetic field in the magnetic resonance volume, radio frequency signals are applied so as to elicit magnetic resonance signals from tissues of the subject in the magnetic resonance volume. The method further includes the step of receiving these magnetic resonance signals and deriving magnetic resonance information relative to the subject's tissues in the magnetic resonance volume from the magnetic resonance signals. Further, the method includes the step of actuating the movable energy-applying device to apply energy to tissues of the patient in the energy application zone so as to treat the tissues and controlling one or more parameters of the treatment by use of the magnetic resonance information.

As mentioned above in connection with the apparatus, the use of movable static field magnets and energy applicators allow these devices to be positioned relative to the patient. Here again, it is preferred to use a static field magnet and energy applicator which are mounted to a common chassis, so that the positioning steps include the step of moving the chassis so as to position the chassis relative to the subject. The chassis may be moved after the procedure so as to reposition the magnetic resonance volume and energy application zone in a new region of the subject and the remaining steps of the procedure may be repeated so as to treat the tissues in a new region. The methods according to this aspect of the invention also include the realization that because the treatment procedure is localized, it can be performed using a magnet with a relatively small magnetic resonance volume.

Most preferably, the magnetic resonance signals are spatially encoded, and the step of deriving magnetic resonance information is performed so as to derive magnetic resonance information at one or more points within the magnetic resonance volume, the points having locations defined in the local magnetic resonance frame of reference. The parameter or parameters of the treatment which are controlled using the magnetic resonance information may include the location of the treated tissues. Thus, the monitoring step may include the step of controlling the location of the treated tissues in a working frame of reference which is correlated to the local magnetic resonance frame of reference. Thus, the step of controlling the location of the treated tissue may include the step of aiming the energy applicator so as to apply the energy at one or more treatment locations having positions defined in the working frame of reference. The aiming procedure may involve either moving the applicator or, in the case of a phased array applicator, adjusting the phases and amplitudes of the signals supplied to the elements of the array. The method may farther include the step of displaying an image of the subject's tissues in a working frame of reference, desirably the local magnetic resonance frame of reference. The image desirably is derived in whole in part from the magnetic resonance information obtained by use of the movable static field magnet and associated components. The aiming step may be performed at least in part by inspection of the image as, for example, by observation of a representation of the aim of the energy applicator superposed on the image.

According to a further aspect of the invention, a method of treating a mammalian subject may include the step of selecting a treatment volume within the subject having boundaries defined in a working frame of reference.

A method according to this aspect of the invention may also include the steps of actuating the applicator to apply energy at a plurality of test points in or adjacent the treatment volume and determining a degree of heating of the tissue at each such test point resulting from such actuation. Most preferably, the method further includes the step of deriving a relationship between energy applied by the applicator and degree of heating for a plurality of treatment locations within the treatment volume from the degrees of heating of the test points and the energy applied by the applicator to the test points. A method according to this aspect of the invention desirably further includes the step of actuating the applicator to apply energy at the treatment locations, the amount of energy applied by the applicator in this step at each such treatment location being selected at least in part on the basis of the relationship between energy and heating for such treatment location derived in the aforesaid steps. This method may be used in magnetic resonance-guided hyperthermia including the aforesaid methods using the movable static field magnet, and other methods. The step of determining degrees of heating for the test points desirably includes the step of acquiring magnetic resonance information for each such test point. The test doses of energy desirably are applied at levels less than a threshold level required to cause permanent change in the tissues at the test points. The step of deriving the energy to heating relationship for the treatment locations desirably includes the step of deriving a relationship between energy supplied and degree of heating for each test point and interpolating between such relationships over distance between the test points. In a particularly preferred arrangement, the boundaries of the treatment volume include one or more polyhedral primitives and the test points are disposed adjacent vertices of the polyhedral primitives. The boundaries may be selected by displaying an image of the subject in the working frame reference encompassing the region to be treated, displaying a visual representation of the boundaries superposed on the image and applying manual inputs to a control element to adjust the boundaries while the visual representation is displayed.

After the boundaries have been established, some or all of the remaining steps desirably are performed automatically. Thus, the step of actuating the applicator to apply the therapeutic energy at the treatment locations may be performed by automatically adjusting the aim of the applicator to different treatment locations within the preset boundaries according to a preselected sequence such as a sequential raster scan or a pseudorandom pattern and automatically operating the applicator to apply the appropriate therapeutic dose. Methods according to this aspect of the present invention greatly facilitate the therapeutic process. They provide good control over the therapy and compensation for the varying response to applied energy at different points within the body while greatly minimizing the time spent in determining the susceptibilities at various points and the effort required to perform the procedure.

Yet another aspect of the present invention provides a method of therapy including the steps of defining an avoidance zone encompassing the tissues of the subject which are not to be subjected to treatment in a working frame of reference and recording the boundaries of the avoidance zone. A method according to this aspect of the invention also includes the step of operating an intrabody treatment device such as an energy applicator by manually moving an aim point of the treatment device relative to the subject and manually actuating the treatment device to apply a treatment at the aim point. Methods according to this aspect of the invention also include the step of tracking the aim point in the working frame of reference during the manual operation step and automatically controlling operation of the treatment device so as to preclude application of the treatment in the avoidance zone. The step of automatically controlling operation may include the step of automatically inhibiting movement of the aim point into the avoidance zone. For example, the step of manually moving the aim point may include the step of manually moving an actuator such as a joystick and the step of automatically inhibiting movement of the aim point may include the step of providing force feedback opposing movement of the actuator in a direction corresponding to movement of the aim point into the avoidance zone when the aim point is near the avoidance zone. Alternatively or additionally, the step of automatically controlling operation of the treatment device may include the step of inhibiting application of the treatment when the aim point is in the avoidance zone. For example, where the treatment device is an energy applicator, the automatic control may inhibit application of energy if the aim point is in the predefined avoidance zone. The avoidance zone may be defined in a manner similar to the treatment volume discussed above, i.e., by displaying a visual representation of the image of the subject and displaying a visual representation of the boundaries of the avoidance zone superposed on such image while applying manual inputs to a control element to adjust the boundaries. Methods according to this aspect of the present invention provide greatly enhanced safety in manually controlled therapeutic procedures such as thermal ablation of tissues. These and other features and advantages of the present invention would be more readily apparent from the detailed description of the preferred embodiments set forth below, taken in conjunction with the accompanying drawings.

BRIEF DESCRIPTION OF THE DRAWINGS

FIGS. 7 and 8 are diagrammatic representations of screen displays during certain methods in accordance with the invention.

FIG. 13 is a diagrammatic perspective view depicting apparatus in accordance with yet another embodiment of the invention.

DETAILED DESCRIPTION OF THE PREFERRED EMBODIMENTS

Figure 1:
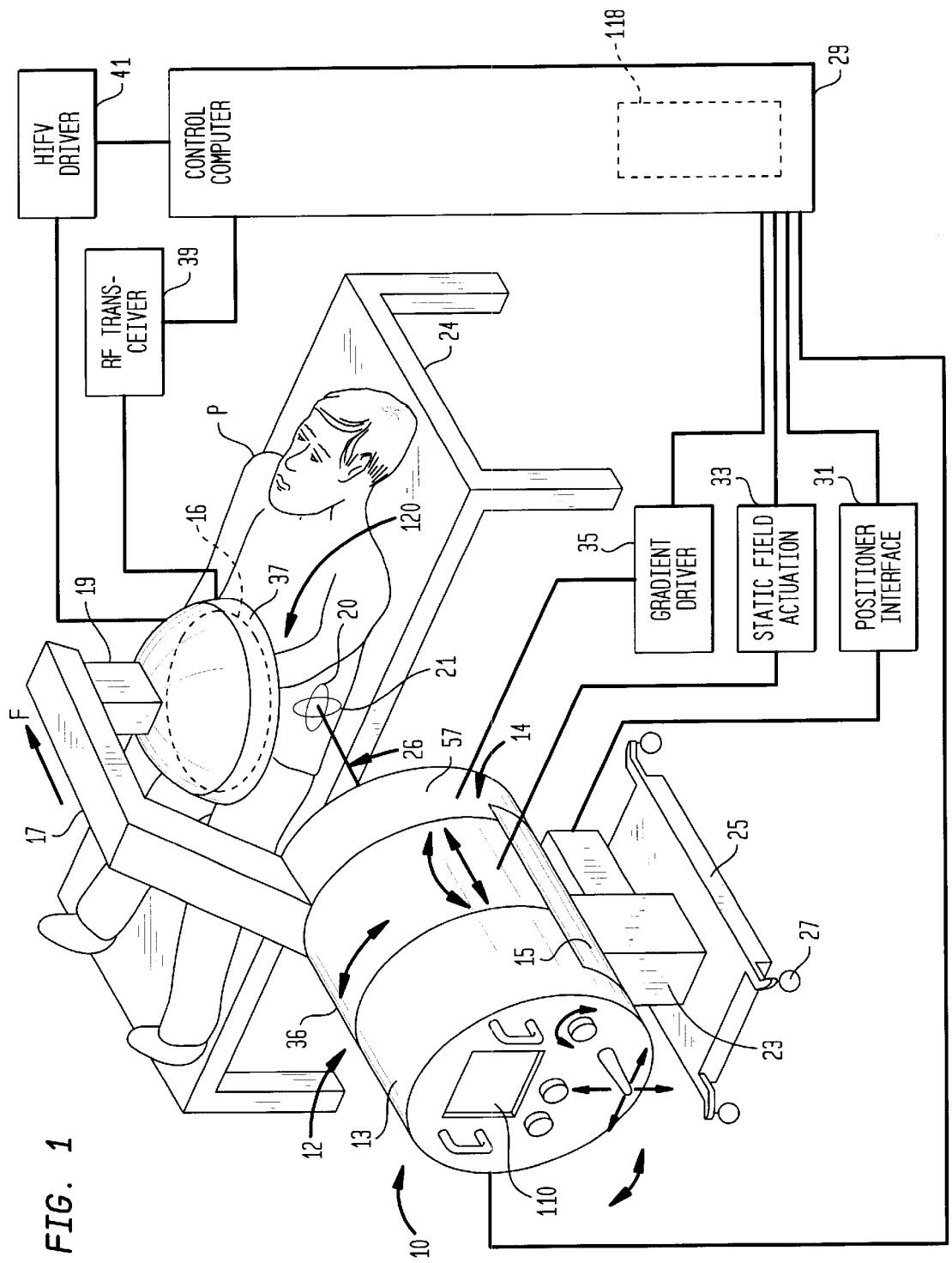
FIG. 1 is a perspective, partially block diagrammatic view depicting apparatus in accordance with one embodiment of the invention.

Apparatus in accordance with one embodiment of the invention includes a mobile unit 10 incorporating a static field magnet 12, gradient coil assembly 14 and a command and control console 13 all mounted to a common chassis 15. The chassis 15 includes an arm 17 projecting upwardly from the other components and projecting in a forward direction indicated by arrow F in FIG. 1. A mounting socket 19 at the forward end of arm 17 carries a disposable high-intensity focused ultrasound or "HIFU" emitter 16. As further explained below, the static field magnet 12 is arranged to provide a suitable magnetic field for magnetic resonance imaging within a magnetic resonance volume disposed forwardly of unit 10, whereas the HIFU unit 16 is arranged to apply ultrasonic energy at selected focal points within an energy application zone 21 intersecting magnetic resonance volume 20. Chassis 15 is mounted on a positioning system 23. The positioning system 23 is supported on a base 25. Base 25 in turn is provided with casters 27. Casters 27 can be extended so that the entire mobile unit 10 and base 25 can be moved across the floor of the room and can be brought into close alignment with a desired region of a patient pier lying on a bed 24. Once the unit is roughly aligned with the desired region, the casters may be retracted and the unit may be brought into the desired, more precise alignment using the positioning system 23 as discussed below. Casters 27 may be replaced by slides, air cushion supports. Positioning system 23 includes conventional devices such as hydraulic or pneumatic actuators, screw jacks and rotary movement devices for moving chassis 15 in multiple degrees of freedom including translation in all vertical and horizontal directions and rotation about three orthogonal axes. Positioning system 23 also includes conventional drive components such as servo motors for driving mechanical linkages and pumps for driving hydraulic or pneumatic movement devices. Moreover, the positioning system desirably includes conventional feedback control elements such as potentiometers and optoelectronic encoders for providing signals indicating the relative positions of the movable elements in the positioning system and thereby indicating the position and orientation of the chassis 15. For example, where transitional or pivoting movement of the chassis in one degree of freedom is controlled by a screw mechanism, the screw shaft may be provided with a conventional digital encoder for detecting and reporting the positions of the shaft. Control console 13 is linked to a control computer 29. The control computer is also linked through a positioner interface 31 to positioner 23. The positioner interface includes conventional components for converting signals sent by the feedback control components of the positioner into the digital format used by the control computer, and for converting signals from the control computer into driver signals for the positioning system. A static field actuation unit 33 controls the currents in the coils of the static field magnet 12, whereas a gradient driver 35 actuates the gradient coils 14 to impose magnetic field gradients as discussed below. A radio frequency antenna 37 is mounted around the HIFU unit 16 and linked to an RF transceiver 39. The transceiver 39 is also controlled by control computer 29. Further, an electrical driver 41 is connected to HIFU unit 16. Driver 41 is also controlled by control computer 29. As further discussed below, these components cooperate to perform magnetic resonance imaging within magnetic resonance volume 20 and to apply ultrasonic energy at selective points in energy application volume 21.

The Static Field Magnet

Figure 2:
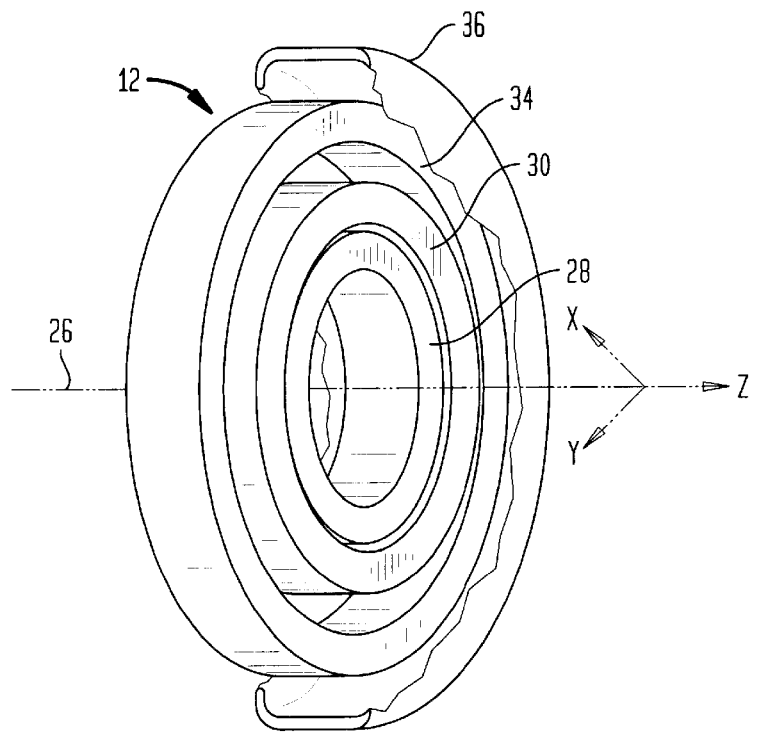
FIG. 2 is a diagrammatic perspective view depicting portions of a magnet incorporated in the apparatus of FIG. 1.

As best seen in FIG. 2, static field magnet assembly 12 includes a plurality of cylindrical superconductive coils concentric with a central axis 26. The coils include an inner coil 28; middle coil 30; and outer coil 34 arranged concentrically with one another. A toroidal cryostat 36 encloses these coils. As best seen in FIG. 1, cryostat 36 defines an interior bore 38 extending through the innermost coil 28 and encompassing axis 26. Cryostat 36 is formed as a toroidal shell of a non-ferromagnetic material. The cryostat contains a coolant such as liquid helium or liquid nitrogen for maintaining the coils at superconducting temperatures. In a known manner, the coils are supported within the cryostat by internal supports (not shown). Although the wall of the cryostat is illustrated as a simple wall, in actual practice the cryostat desirably has one or more multiple wall structures with evacuated spaces between the walls. Such a structure is also referred to as a Dewar vessel and minimizes heat conduction to the contents of the cryostat, including the coils and the coolant. Alternatively, the cryostat may be an insulated enclosure which is cooled by means other than cryogenic fluids, such as by thermoelectric cooling or other conventional refrigeration systems. These systems can be used with high $T_c$ superconductors.

Figure 3:
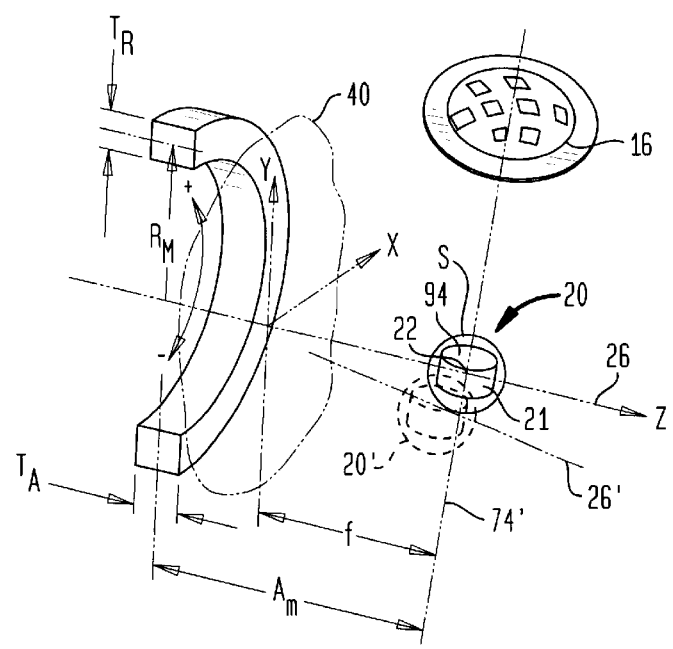
FIG. 3 is a diagrammatic view depicting still further portions of the apparatus of FIGS. 1 and 2.

The frame of reference and dimensioning system used to denote the dimensions of the individual coils are illustrated in FIG. 3. The mean radius or $R_m$ and radial thickness $T_r$ of each coil are specified with respect to the central axis 26. The axial placement of each coil is given as the mean axial dimension $A_m$ of the coil, measured from the center point 22 of the magnetic resonance volume. The axial thickness $T_a$ of each coil is the dimension of the coil parallel to axis 26. The coil also defines a frontal plane 40 perpendicular to axis 26 at the forwardmost extent of the forwardmost coil in the static field magnet assembly.

The coils of magnet 12 are connected to a conventional current source or static field actuator unit 33 (FIG. 1). Unit 33 provides currents in the coils. The directions of current flow in the various coils are denoted as "positive" or "negative" symbols" as indicated by the arrows in FIG. 3. These arbitrarily-selected directions of current flow are opposite to one another. The forward spacing distance f or distance from the frontal plane of the static field magnet assembly to the center point 22 of imaging volume 20 is also illustrated in FIG. 3.

The dimensions of the coils for the exemplary embodiment shown in FIGS. 1, 2 and 3 are set forth in Table I below.

TABLE I

| Coil | Current Sense | Ampere Turns | Axial Location $A_m$ (cm) | Axial Thickness $T_a$ (cm) | Mean Radius $R_m$ (cm) | Radial Thickness $T_r$ (cm) |
|---|---|---|---|---|---|---|
| Inner (28) | Positive | 1,159,200 | 33.7 | 14 | 17.88 | 5.04 |
| Middle (30) | Negative | 1,863,000 | 33.7 | 14 | 25.55 | 8.1 |
| Outer (34) | Positive | 1,076,400 | 33.7 | 14 | 36.64 | 4.68 |

As indicated, the magnet provides a field of approximately 1 kilogauss with a relatively small linear axial field gradient $$\frac{dB}{dZ}$$

within a region about 5 cm in diameter at about 25–30 cm from the frontal plane. In this same region, the radial field curvature $$\frac{d^2B}{dX^2}$$

is also relatively small and hence the field gradient in the radial direction is also relatively small. The magnet provides a field with a linear axial gradient and with very small radial gradients over a magnetic resonance volume or imaging volume 20 having axial extent of about 1 cm and having a diameter of about 3 cm. The volume 26 centered on point 22 at a forward spacing distance f from the frontal plane 40 of about 26 cm. The magnet is relatively small; the coils of the magnet can be accommodated in a cylinder approximately 78 cm in diameter and only about 14 cm thick. The small dimensions of the magnet dramatically reduce the cost and weight of the cryostat, and the cost of operation. Depending upon the materials used for the cryostat, the entire magnet may have a mass of less than about 500 kg and hence can be moved and positioned relative to the patient by a positioning device 23 of reasonable size.

The Gradient Coil Assembly

Figure 4:
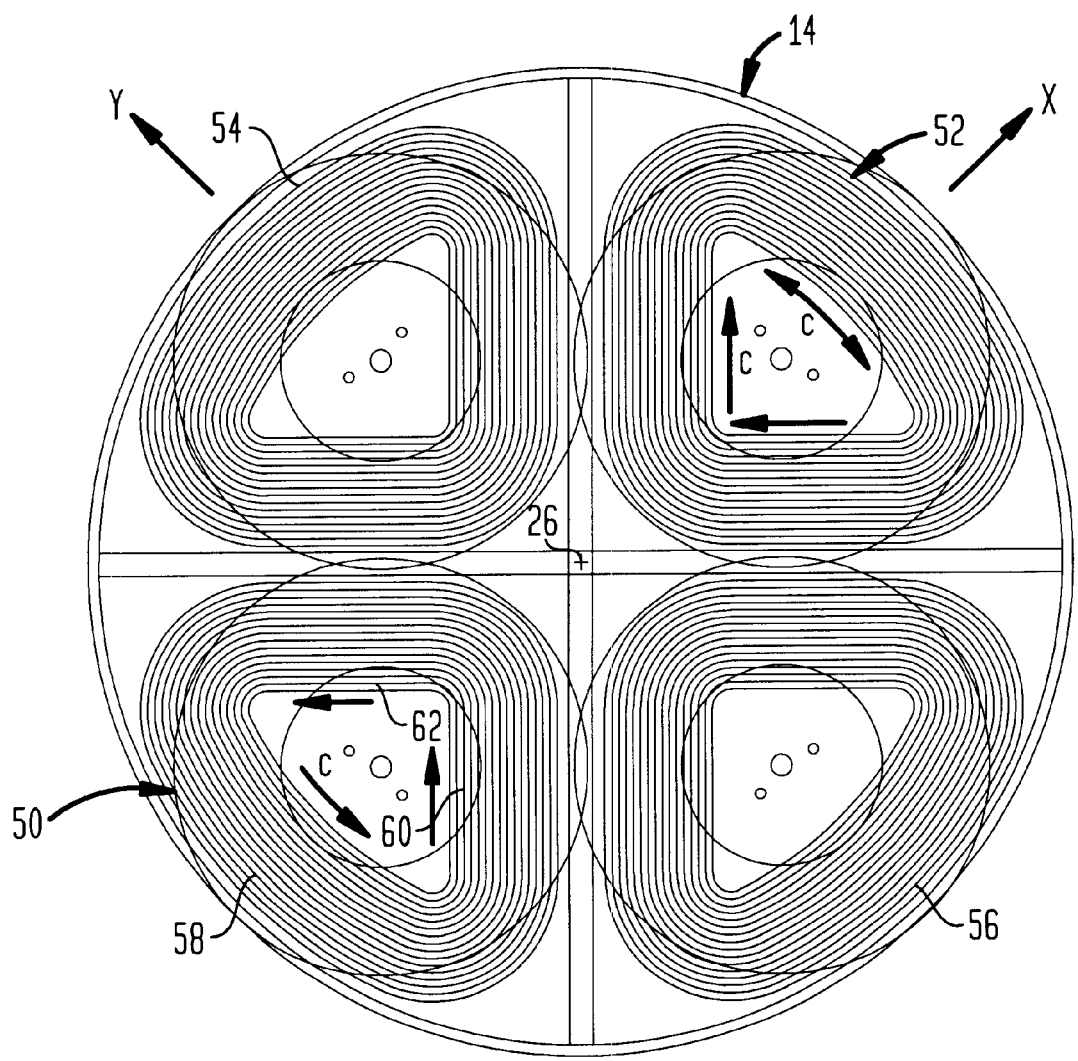
FIG. 4 is a diagrammatic elevational view depicting gradient coils employed in the apparatus of FIGS. 1–4.

The gradient coil assembly 14 is depicted in FIG. 4. The gradient coil assembly includes four windings 50, 52, 54 and 56 disposed around the common or central axis 26 of the static field magnet so that windings 50 and 52 form one diametrically opposed pair of windings and windings 54 and 56 form another diametrically opposed pair. The windings are generally planar and lie generally in plane perpendicular to the axis 26 of the static field magnet. Coils 50 and 52 are disposed along a first axis (labeled "X" in FIG. 4) perpendicular to the central axis 26 or Z-direction of the static field magnet 12, whereas the other pair of windings 54 and 56 are disposed along another axis (labeled "Y" in FIG. 4) perpendicular to the central axis 26 or Z-direction and perpendicular to the X axis of windings 50 and 52. The windings are formed from metallic ribbon having a small thickness dimension and a larger width dimension, the ribbon being wound on edge so that the width wise direction of the ribbon extends perpendicular to the plane of the winding and hence parallel to the axis 26. For example, the ribbon may be about 0.016 inches (0.4 mm) thick and about 0.75 inches (2 cm) wide. Each winding may include about 120 turns of such ribbon. Winding 50 includes an outer arcuate run 58 generally in the form of a circular arc concentric with axis 26, and also includes a pair of radial runs 60 and 62 extending generally radially inwardly from the ends of the arcuate run 58. These runs merge with one another adjacent central axis 26. Each of the other coils 52, 54 and 56 includes similar runs. Because the static field magnet inherently imposes a field gradient in the axial or Z direction, the gradient coil assembly used in this embodiment does not include a Z-direction gradient coil. However, if a Z-direction gradient coil is required, the same may be as a circular solenoid concentric with central axis 26.

The windings are mounted in a non-ferromagnetic housing 57 which is provided with cooling passages (not shown) connected to a chiller or other source of coolant. The radius from the central axis 26 to the outside of the outer arcuate run of each winding desirably is about 25 cm or less so that the entire gradient coil assembly 14 and housing 57 is only about 50 cm diameter and about 3–4 cm thick.

Housing 57 is disposed immediately in front of the static field magnet 12, i.e., just forward of the cryostat 36 and as close as possible to the frontal plane 40 of the static field magnet. This leaves a large unoccupied region along the axis 26 between the gradient coil assembly and the imaging volume 20, so that the imaging volume can be positioned deep within the patient's body. The windings of the gradient coil assembly are connected to gradient driver 35. The power and control leads to the gradient coils may extend through the bore of cryostat 36.

The gradient driver includes conventional D/A converters and amplifiers for receiving a desired gradient waveform in digital form from computer 29, converting the digital waveform to analog form and reproducing the analog waveform as currents in particular gradient coils controlled by the computer of the apparatus. To apply a magnetic field gradient in the X-direction within the imaging volume 20, the two windings of a pair may be energized so that the current flows in the outer arcuate runs of both windings in the opposite directions around the axis 26 of the static magnetic field assembly. For example, when windings 50 and 52 are energized with the current flows as indicated by arrow C in FIG. 4, they will provide a field gradient in one direction in the X axis. The reverse current flows will produce a gradient in the opposite direction. Windings 54 and 56 can be actuated in the same manner so as to impose a field gradient in the Y-direction.

The HIFU Unit and RF System

The socket 19 at the forward or distal end of arm 17 includes a mechanical mounting element 62 (FIG. 5) such as the tapered bore illustrated or any other conventional device for making a releasable mechanical interengagement. For example, the tapered bore 62 may be replaced by a conventional vise, clamp, bolt joint or gripper, a multi-jawed chuck or a collet chuck. Mounting 19 also includes a coolant supply passage 63 and coolant withdrawal passage 64 which are connected to a conventional source (not shown) of a coolant such as chilled water. Mounting 19 further includes a multi-element electrical connector 66 which in turn is connected to the high intensity focused ultrasound driver 41 (FIG. 1).

The ultrasonic energy applicator 16 includes a disposable high intensity focused ultrasound unit 68. Unit 68 includes a substantially rigid frame 70, desirably formed from a polymeric material such as a polycarbonate or epoxy or other relatively rigid, high strength polymer. Frame 70 has a mounting element 72 rigidly connected thereto. The mounting element 72 is adapted to mate with the mounting receptacle 62 to form a rigid yet releasable connection. For example, where the mounting receptacle includes a tapered socket, mounting element 72 may be a pin having a mating taper. Frame 70 defines a shallow dish generally in the form of a surface of revolution about an axis 74.

Figure 6:
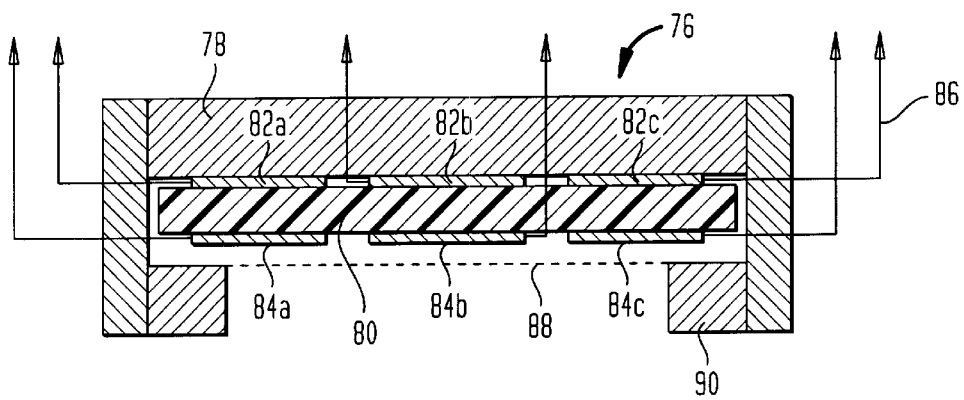
FIG. 6 is a diagrammatic sectional view depicting a portion of the ultrasound unit shown in FIG. 5.

A plurality of ultrasound emitting sections 76 are disposed in a array on frame 70. As best seen in FIG. 6, each section 76 includes a rigid backing 78 such as a block of alumina, glass or rigid polymer. The section also includes a piezoelectric film 80 such as a polyvinylidene fluoride film of the type sold under the registered trademark Kynar by AMP Inc. of Harrisburg, Pa. A set of rear electrodes 82 is provided between film 80 and the backing 78, whereas a set of front electrodes 84 is provided on the front surface of film 80 facing away from backing 78. The front and rear electrodes are provided in matched pairs, so that the front electrode of each pair overlies the rear electrode of each pair. For example, electrodes 82(*a*) and 84(*a*) form a pair. These electrodes are aligned with one another and overlie with one another. Although only three pairs of electrodes are visible in FIG. 6, the emitter section 76 may include numerous pairs of electrodes arranged in an array, as, for example, a three by three array incorporating nine pairs. A separate lead extends to each electrode. Electrodes 82 and 84 desirably are formed as thin conductive deposits on the surfaces of piezoelectric film 80 as, for example, by applying an electrically conductive ink on the surfaces of the piezoelectric layer or by processes such as sputtering or electroless plating, followed by electroplating. Individual leads 86 extend from each of the electrodes.

Each pair of electrodes, and the portion of film 80 disposed between such pair of electrodes films an independently operable piezoelectric transducer. By applying opposite voltages to the two electrodes of the pair, the region of the film between the electrodes can be made to expand or contract in the forward to rearward direction, i.e., in the direction towards the top and the bottom of the drawing as seen in FIG. 6. Thus, by applying an alternating potential, the portion of the film between each pair of electrodes can be driven at ultrasonic frequencies. The particular section illustrated has the rear electrodes directly bonded to the surface of backing 78 so that the rear electrodes and the rear surface of the film are held rigidly. In this arrangement, it is desirable for the thickness of the film 80 to be approximately one-quarter of the wavelength of the ultrasonic vibrations. Typical operating frequencies are in a range of about 1 to 1.8

MHz, most commonly about 1.5 MHz, and the wavelength of the ultrasonic vibrations in the film is about 1 mm. Thus, where the rear surface of film is rigidly held to the backing as in the embodiment of FIG. 6, the preferred thickness of film 80 is about 250 microns. In other embodiments, the film is supported away from the backing, so that the rear surface of the film is spaced from the backing and is free to vibrate. In these embodiments, the thickness of the film is approximately one half wavelength and desirably is about 500 microns or more. Protective layers (not shown) such as a thin polymeric film or encapsulant may be provided over the front surfaces of film 80 and electrodes 84 to protect them from contact with the environment. A ring 90 formed from a rigid material such as alumina or polymeric material extends around the periphery of the film. Ring 90 is secured to support 78.

Figure 5:
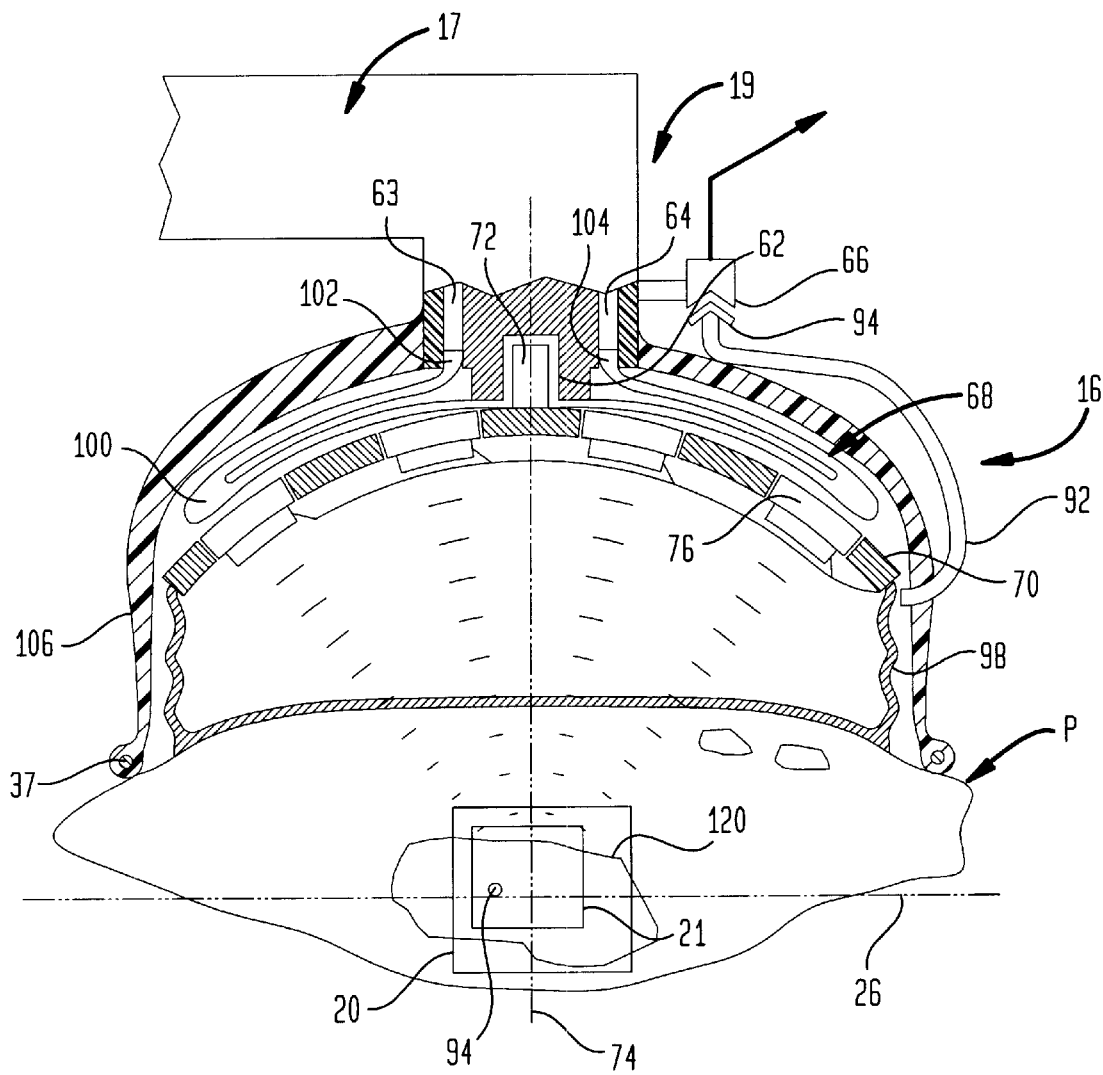
FIG. 5 is a diagrammatic sectional view depicting a high intensity focused ultrasound unit and associate components used in the apparatus of FIGS. 1–4.

Sections 76 are secured to the frame 70 (FIG. 5). The individual leads associated with the various electrodes of all of the sections are connected through a common cable 92 to a multi-element plug 94 adapted to mate with multi-element socket 66 of mounting 19. The individual leads and cable 92 are constructed using standard techniques applicable to electrical structures for frequencies on the order of 1.5 MHz. For example, the individual leads to each pair of electrodes desirably are provided as a coaxial, twisted pair or other transmission line suitable for high frequency operation. Also, cable 92 may be formed as a so-called flex circuit capable of accommodating a large number of transmission lines. The individual sections 76 are mounted in the frame so that the forward or active surface (the surface bearing forward electrodes 84) faces forwardly, i.e., in the downward direction as seen in FIG. 6. The front faces of the elements are directed generally inwardly towards an applicator axis 74 as well as forwardly. The individual elements of the sections thus constitute a phased array of ultrasonic emitters. The energy emitted by the various ultrasonic emitters can be focused into a small focal spot 94. Desirably, the array is optimized to provide a spot having dimensions on the order of about 2–3 mm. Where the device will be used for thermal ablation, the array desirably provides an ultrasonic intensity of approximately 1500 watts/cm$^2$ at the focal spot to enable heating of tissues at the focal spot from about 37° C. to about 60–80° C. in less than one second. Such rapid heating capability greatly reduces treatment time. Typically, approximately 1500 watts of electrical power must be applied to the array to yield about 500 watts of ultrasonic emission. The focal spot can be provided over a range of positions within energy application volume 21. The focal spot can be moved within energy application volume 21 by varying the phases and amplitudes of the driving signals applied to the individual ultrasonic emitting elements, i.e., by varying the phases and amplitudes of the electrical signals sent to the various electrodes 82 and 84.

The size and shape of the focal spot, as well as the range of positions over which the spot may be moved depends on the relative placement and properties of the emitters. Desirably, the array is arranged to provide a focal length of about 20 cm, i.e., the distance from the array to the center of the energy application volume 21 along axis 74 is about 20 cm or more. Typically, the array has a diameter of about 15 cm. The particular arrangement discussed above is merely exemplary. Thus, the individual sections may be flat as discussed above, or else may be curved. Curved sections may have a generally spherical shapes, or else may may have different radii of curvature along differenct axes. The sections may be smaller or larger than those discussed above. At one extreme, each section may include only one element. At the other extreme, the entire array can be formed as a single curved section and the backing of such section can serve as the frame 70. The individual emitting elements within the array, and the individual emitting elements within a single section, may have different shapes and sizes. For example, the emitting elements may have square or other polygonal shapes, or may have circular or elliptical. The design of ultrasonic phased arrays, and computer simulations of such arrays are disclosed in Ebbini, et al., Optimization of the Intensity Gain of Multiple-Focused Phased Array Heating Patterns, Int. J. Hyperthermia, 1991, Vol. 7, #6, pp. 953–973; Ebbini et al., Multiple-Focused Ultrasound Phased-Array Pattern Synthesis: Optimal Driving Signal Distributions for Hyperthermia, IEEE Transactions on Ultrasonics, Ferro Electrics and Frequency Control, Vol. 36, pp. 540–548 (1989) and Fan et al., Control Over the Necrosed Tissue Volume During Non-Invasive Ultrasound Surgery Using a 16-Element Phased Array, Medical Physics, Vol. 22 (#3), pp. 297–305 (1995). The disclosures of these articles are hereby incorporated by reference herein.

The disposable unit 68 further includes a flexible water-filled bag 98 attached to the frame 70 so that the ultrasonic emitting elements on the frame are coupled to the water for transmission of ultrasonic emissions into the water. For example, the bag may be attached to the periphery of frame 70. Bag 98 may be formed from a thin polymeric film. For example, the surface of the bag which will lie against the subject's body in use may be formed from a polyethylene terepthalate film, whereas the other walls of the bag may be formed from a polyethylene film. Preferably, the water within bag 98 is substantially free of dissolved air. If the film constituting bag 98 is air-permeable, it is preferably to remove air from the water during manufacture of the disposable unit, and to supply the disposable unit vacuum-packed in an outer container which is air-impermeable. The disposable unit also includes a coolant passage 100 having connectors 102 and 104 adapted to fit the coolant passages 63 and 64 of mounting 19. The HIFU driver 41 (FIG. 1) includes conventional components for providing the required driving signals as commanded by computer 29. Driver 41 is connected to receptacle 66 so that when cable 92 is connected to the receptacle, the HIFU driver is connected to all of the individual electrodes 82 and 84 of the piezoelectric elements.

A flexible skirt 106 is mounted permanently on the distal end of arm 17 so that it surrounds mounting 19 and so that the skirt projects downwardly away from arm 17. The circular loop antenna 37 is mounted to the edge of the skirt remote from the arm. RF transceiver 39 is connected to loop antenna 37. The transceiver typically includes a relatively high powered transmitting section and a sensitive receiver, together with devices for disabling the receiver when the transmitter is actuated and vice versa. The RF antenna and transceiver desirably is tunable over a range of frequencies corresponding to the range of Larmor frequencies or magnetic resonance frequencies for protons subjected to the magnetic fields of the static field magnet. Desirably, transmitter and receiver are provided with variable components such as variable capacitors or capacitor switching networks for adjusting or tuning to match the Larmor frequencies at particular locations within the imaging volume.

In use, the disposable HIFU unit 68 is received within skirt 106 and engaged with mounting 19 so that the HIFU unit is held physically on arm 17 with the axis 74 of the HIFU unit projecting generally downwardly and hence transverse to the central axis 26 of the static field magnet. In this condition, the energy application volume 21 overlaps the imaging volume 20. Moreover, the HIFU unit is rigidly held at a fixed position and orientation with respect to the static field magnet. When the unit is operated with patient P, the arm 17 desirably is positioned so that the water bag 98 is engaged with the patient's skin. Ultrasonic vibrations may be transmitted from the piezoelectric elements of section 76 through the water within a bag 98 and through the bag itself into the patient with minimal losses. A gel or cream may be applied at the surface of the bag to minimize transmission losses. Loop antenna 37 is disposed in or near the patient's body surface. The axis of the loop antenna is close to or coincident with the axis 74 of the HIFU unit. Stated another way, the axis of loop antenna 108 is transverse to the central axis 26 of the static field magnet, and hence transverse to the magnetic field vector.

The Control Console and Control Computer

Control console 13 includes a conventional monitor 110 such as a cathode ray tube or flat panel display, as well as manual input devices including a joystick 112 (FIG. 7) and a rotatable dial 114. Joystick 112 desirably is a so-called "force-feedback" joystick, equipped with conventional devices for applying forces to the joystick responsive to commands received by the joystick assembly. One suitable joystick is sold under the trademark Sidewinder Force Feedback Pro by Microsoft Corporation. Dial 114 may be incorporated in the joystick assembly. The joystick is also equipped with a push button 115.

The control console further includes additional command and control switches 116, and may further include a keyboard (not shown). All of these elements are linked to control computer 29. Control computer 29 (FIG. 1) desirably is a conventional general purpose digital computer such as a computer of the type commonly referred to as a "workstation" and includes conventional elements such as microprocessor and data transfer bus (not shown). The control computer further includes memory elements 118, which may incorporate conventional devices such as dynamic random access memory, flash memory or the like and mass storage such as magnetic disc optional storage. The data bus of the control computer is linked through a conventional interfacing element (not shown) to the elements of the control console; to the positioner interface; to the static field application unit 33 and gradient driver 34 and to the HIFU driver 41 and RF transceiver 39. The control computer program desirably is arranged to display a menu of operating modes as discussed below on monitor 110, so that the operator can select the desired operating mode by activating switches 116.

Operation

In a method according to an embodiment of the invention, a patient P (FIG. 1) is supported on a bed 24. Mobile unit 10 is moved on castors 27 into a position such that the magnetic resonance volume 20 and energy application volume 21 are approximately aligned with the organ 120 of the patient which requires treatment. The water-filled bag of the HIFU unit is engaged with the patient's skin and the RF antenna 37 is positioned around the bag. The operator actuates the computer to perform a preliminary magnetic resonance imaging operation. Thus, the static field magnet is operated to apply the magnetic field within magnetic resonance volume 20 and the gradient coils and RF transceiver are operated to apply RF signals and magnetic field gradients in a conventional magnetic resonance imaging sequence. Transceiver 39 and antenna 37 are tuned to a frequency corresponding to the Larmor frequency by atomic nuclei, preferably protons at the magnetic field prevailing in a particular thin slice S (FIG. 3) within magnetic resonance volume 20. Because the magnetic field provided by the static field magnet incorporates a gradient in the axial or Z direction and because the Larmor frequency of the nuclei varies proportionally with the prevailing magnetic field, the resonant or Larmor frequency varies with distance along the Z axis. In the conventional manner, the transceiver is actuated to send a pulse of RF energy into the subject, thereby exciting the nuclei within the slice S where the resonant frequency of the nuclei matches the frequency of the RF signal. Also, in a conventional manner, the gradient coils are actuated to apply magnetic field gradients in the X and Y directions, transverse to the axial or Z direction. This causes the signals from the nucleii at various positions within the slice to vary in frequency and phase in a known manner. The RF transceiver is actuated to receive the magnetic resonance signals and to digitize the same and supply the digitized signals to control computer 29. This process is repeated with variation of the X and Y gradients in known fashion. The signals acquired by transceiver 39 are stored in the memory of the computer. Using known procedures, the control computer reconstructs an image of the subject's tissues within slice S. This procedure can be repeated again using different radio frequencies so as to select different slices within magnetic resonance volume 20. The resulting data provides a three dimensional image of that portion of the subject located within the magnetic resonance volume.

The image is displayed on monitor 110. The operator can observe the image and determine whether the region of the subject to be treated is centered in the field of view. As depicted in FIG. 7, the image may be displayed as a pair of orthogonal sectional views through the subject. If the region requiring treatment is not centered in the field of view, the operator can enter a command to the control computer, to enter a repositioning mode. In this mode, the computer accepts input from the joystick 112 and dial 114. Thus, depending upon the commands received from the command input element 116, the control computer will interpret input from joystick 112 and turn wheel 114 as commanding movement of chassis 15 either in translation or in rotation. For example, the computer may be set to accept translation inputs and to treat joystick movements in a direction X' as commanding upward translation of the chassis; joystick movement in a direction Y' as commanding horizontal translation and movement of turn wheel 114 as commanding forward and backward or Z-direction translation of the chassis. After other commands from command input element 116, the computer may treat joystick movements in the X' direction as commanding tilting movements about a horizontal axis transverse to the central axis 26 and joystick movements in the transverse direction Y' as commanding rotation of the chassis around a vertical axis. The imaging procedure is repeated, and the operator continues to monitor the displayed images. As the operator views the images, he or she can use the images to diagnose conditions within the body as, for example, to detect lesions in the body which require treatment. When the organ or region of the body which requires treatment is centered in the field of view, the operator issues a further signal to the command input element 116 which causes the control computer to lock the position and thereby fix chassis 15, the static field magnet, the HIFU unit and other elements in position. Thus, the local magnetic resonance frame of reference established by the static field magnet and associated components is fixed.

Figure 8:
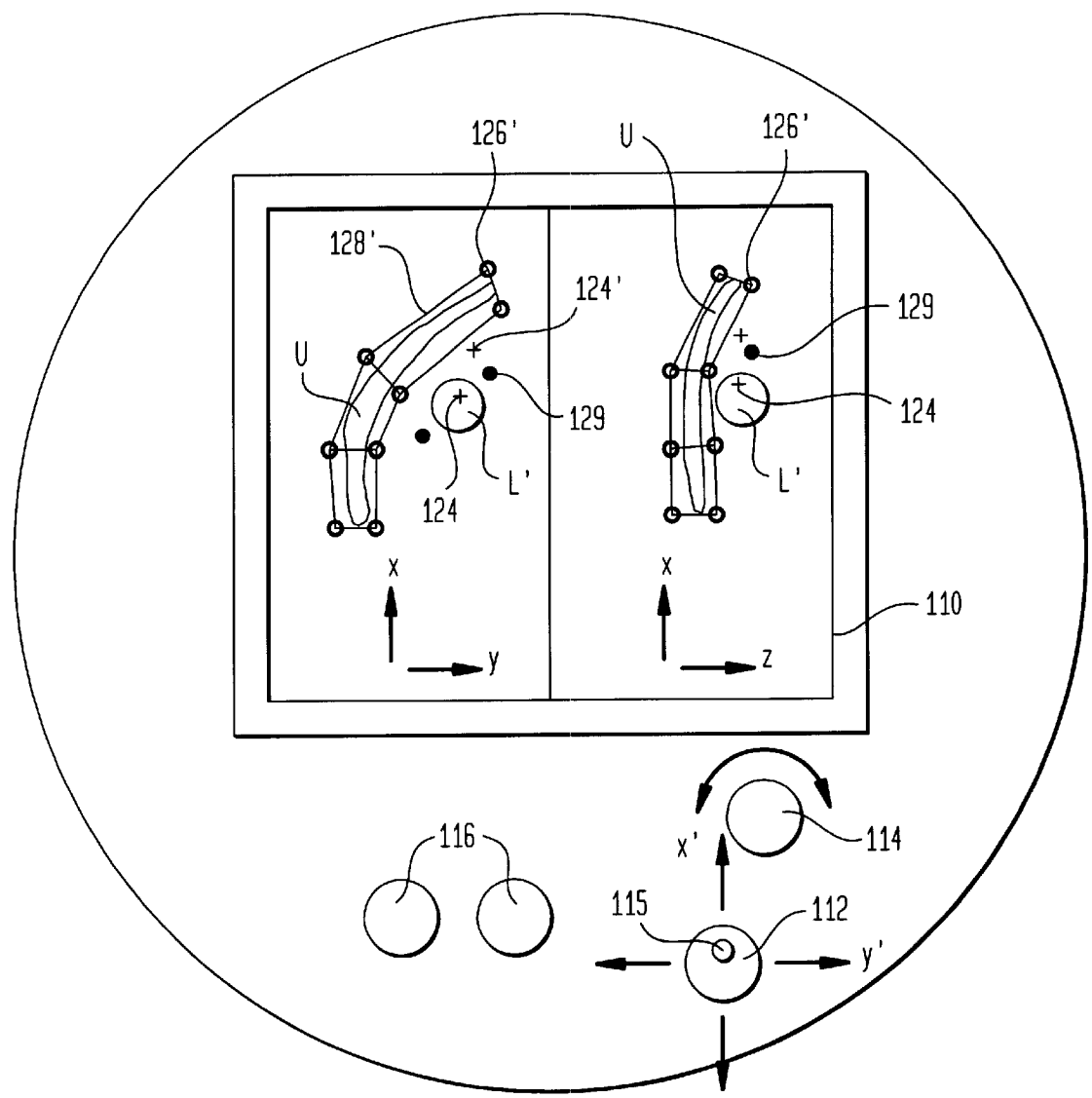

In this condition, the computer treats inputs from joystick 112 and dial 114 as commanding movement of a theoretical aim point in this fixed local magnetic frame of reference. Thus, as the joystick moves in X' and Y' directions, the position of the theoretical aim point changes in the X and Y directions, respectively, whereas rotation of dial 114 causes movement of the theoretical aim point in the Z direction. A cursor 124 is displayed within the images on monitor 110 in a position corresponding to the position of the theoretical aim point. Using the dial and the joystick, the operator moves the cursor 124 to a series of vertex points 126. The operator selects these vertex points so that they constitute to be vertexes of a polyhedron, or set of polyhedrons encompassing the treatment zone to be subjected to heating. In the example illustrated in FIG. 8, the image shows a lesion L. The vertex points 126 are selected to form a pair of truncated pyramids 128a and 128b which cooperatively encompass the lesion L. When the operator brings the cursor to each desired vertex, he issues a further command to the control computer as, for example, by pressing a push button 130 on joystick 112. The computer records the theoretical aim point corresponding to each such vertex in memory 118. The computer further generates a wire-frame image of the polyhedron and vertex on display screen 110 and superposes this image over the image of the subject's tissues derived from the magnetic resonance information.

In the next stage of the process, the computer actuates the energy application or HIFU unit 16 to apply focused ultrasound at a spot 94 at a location corresponding to the location of one of the vertices 126. The computer commands the HIFU driver to apply a relatively small "subthreshold" dose of energy to the tissues in the spot 94. That is, the amount of energy supplied by the HIFU driver is selected so that the heat applied in this operation will not destroy or alter the tissue. For example, in a human subject, the tissue may be heated from normal body temperature (37° C.) to about 40° C. In theory, because the HIFU unit is at a known location and orientation in the local magnetic frame of reference, and because the location of spot 94 varies in a known manner with the signals supplied to the HIFU unit by HIFU driver 41, the heated spot should be positioned exactly at the location commanded by computer 29. In practice, due to inaccuracies in the equipment and refraction of ultrasonic energy by body structures, there will be some deviation between the position of the heated spot commanded by computer 29 and the actual position of the heated spot. After the subthreshold dose has been applied, the imaging procedure is repeated using a magnetic resonance sequence which is temperature sensitive, such as a $T_1$ weighted sequence, so that the displayed image includes a spot 94' depicting the heated spot. The operator then actuates the joystick 116 and dial 114 to position cursor 124 over the spot 94 and provides a further control input for push button 115. The computer thus records the location corresponding to the position of the cursor as the position of the actual heated spot. The computer then subtracts the coordinates of the actual position from the corresponding coordinates of the commanded position. The result is a correction vector. In the succeeding operations, the computer will add this correction vector to all new commanded positions so as to provide a corrected commanded position which will result in heating at the true, commanded location.

Once the correction vector has been obtained, the computer executes a test point sequence. In the test point sequence, the computer commands the HIFU unit to apply a series of subthreshold doses at each vertex 126, so that each vertex serves as a test point. When applying each subthreshold dose, the computer commands the HIFU unit to apply a particular amount of energy to the heated spot of the vertex or test point. The magnetic resonance apparatus is actuated to determine the temperature at each test point before and after application of each subthreshold dose. The computer records the amount of energy applied by the HIFU unit (typically measured as input power supplied to the HIFU unit) and the resulting temperatures rise in memory 118. In this regard, the magnetic resonance imaging apparatus need not complete an entire imaging sequence to measure the temperature. Rather, the magnetic resonance apparatus may be actuated in a known manner to acquire magnetic resonance signals from a signal volume element or "voxel" at the test point being heated. So-called "sensitive-point" magnetic resonance methods are described in Mansfield and Morris, NMR Imaging in Biomedicine, 1982, p. 98. By monitoring a parameter of the magnetic resonance signals which varies with the temperature of the tissues as, for example, the spin-lattice relaxation time $T_1$, the computer can monitor the temperature of the subject's tissues at the vertex or test point 126 being heated. From the recorded applied energies and temperature increases, the computer calculates a calibration curve of applied energy versus temperature rise. In the simplest case, the computer calculates only the slopes of a linear plot of temperature rise versus applied energy.

Once the calibration curves have been obtained for all of the vertices, the operator actuates the computer to enter a treatment mode. The computer commands the HIFU unit to apply energy to the subject's tissues within the treatment volumes or polyhedron 128. The computer commands the HIFU unit to apply a therapeutic dose sufficient to heat the tissue at each treatment location to a sufficient degree to perform the required treatment. Where the treatment consists of thermal ablation, the treatment dose is selected to bring the temperature of the tissue above about 43° C., and typically to about 60–80° C. Other treatments, such as to enhance the effect of drugs or radiation therapy, typically use lower temperatures. The amount of energy to be applied at each treatment location is selected based on an interpolated calibration curve. Thus, the calibration curve for each treatment location is computed by linear interpolation among the calibration curves for the test point vertices of the polyhedral treatment volume. For example, the computer can calculate the distance between each treatment location and the various vertices of the polyhedron encompassing that treatment location and then calculate a weighted average slope $S_{ave}$ according to the formula $$S_{ave} = \frac{\sum_{i=1}^{i=n} \frac{S_i}{d_i}}{\sum_{i=1}^{i=n} \frac{1}{d_i}}$$

where:

$S_i$ is the slope at the $i^{th}$ vertex or test point; and $d_i$ is the distance from the treatment location to the $i^{th}$ vertex or test point.

In the case where the treatment location overlies one test point so that one distance $d_i$ is zero, the computer sets $S_{ave}$ equal to the slope at that test point or vertex. For example, treatment location 136a is close to test point or vertex 126a and far from test point or vertex 126b. The computer will set the slope of the energy versus temperature rise plot at treatment location 136a close to the slope at test point 126a. The computer automatically selects new treatment locations, calculates the slope at the newly selected treatment location and applies the appropriate therapeutic dose until therapeutic doses have been applied at all possible treatment locations within the treatment volume defined by polyhedron 128*a* and 128*b*. Desirably, each treatment location is brought to the desired temperature rapidly, typically in one second or less. Thus, the system can complete the treatment throughout the treatment volume rapidly.

During application of the therapeutic doses, the computer may periodically acquire magnetic resonance information from one or more voxels within the treatment volume and monitor the temperature in such voxel based on this magnetic resonance information. Alternatively, the computer can actuate the magnetic resonance apparatus to conduct a full magnetic resonance imaging sequence using a temperature-sensitive imaging protocol and display an image showing the heated region and the surrounding tissues. The operator may command the system to acquire a new magnetic resonance image after completion of the entire treatment so that the effect of the treatment can be assessed.

In an alternate procedure, the operator moves the theoretical aim point applicator using the joystick 112 and dial 114 so as to move the cursor 124 (FIG. 8) about in the displayed image in the manner discussed above, and actuates button 115 to mark vertices 126'. However, the computer is instructed to record these vertices as vertexes of an avoidance zone rather than as vertexes of the treatment volume. In the same manner as described above, the computer generates a wire frame image of polyhedra 128' with vertexes corresponding to vertexes 126'. The operator selects vertices 126' and thus selects the tissues encompassed by the avoidance zone by observing the displayed image. In the example illustrated in FIG. 9, the image of a sensitive structure such as the urethra U is shown on the display monitor 110. The operator has established the avoidance zone so as to encompass the urethra. The computer records the boundaries of these polyhedra as boundaries of the avoidance zone. The operator manually selects test points 129 outside of the avoidance zone and performs the calibrations step discussed above, so as to calibrate the system for errors in aim of the HIFU unit and to arrive at a applied dose to heating calibration curve for each test point 129. Once again, the test points desirably are selected so that they are at or near the periphery of the lesion L' to be treated.

The operator then commands to enter a manual ablation mode. In this mode, the computer responds to a manual operation of the joystick 112 and dial 114 as commands to move the aim point of the HIFU unit, and the computer responds to manual actuation of the push button on the joystick as a command to apply a therapeutic dose at the current aim point. For example, with cursor 124 positioned over the image of lesion L', the theoretical aim point is within the lesion. Application of a therapeutic dose will heat the tissues at the point within the subject's body corresponding to the aim point. The dose can be selected automatically based upon the dose to heating calibration curves calculated as aforesaid or can be selected manually. If the operator attempts to move the aim point into the avoidance zone, the system will prevent him from doing so. Thus, if the aim point is close to the avoidance zone, and if the operator commands the system to move the aim point into the avoidance zone, the system will not do so. Instead, the system will issue a warning signal by providing force feedback through the control. For example, with the cursor in the position indicated at 124' in FIG. 8, upward movement in the X direction will bring the cursor into the avoidance zone. If the operator attempts to move the joystick 112 upwardly in the X' direction and thus moves the cursor 124' upwardly, the system will apply a countervailing force feedback to resist this motion. Force feedback provides a uniquely intuitive warning to the operator. However, other forms of warning signals may be employed. For example, the system may display an alphanumeric warning on the monitor 110, or may cause the monitor display to flash or may illuminate the cursor in a distinct color. Audible warnings may also be employed.

In a further variant of this system, the computer allows the operator to move the aim point into the avoidance zone, but inhibits application of a therapeutic dose while the aim point is within the avoidance zone. Here again, the system can display any form of tactile visual or audible warning before the operator attempts to apply a therapeutic dose while the aim point is in the avoidance zone.

In the methods discussed above, the magnetic resonance information was acquired in only a single magnetic resonance volume. However, the system can collect magnetic resonance information over a plurality of different magnetic resonance volumes. For example, as shown in FIG. 3 the static field magnets and related components can be swung about a vertical axis so as to swing the central axis 26' to a new orientation and move the magnetic resonance volume to a new position indicated in broken lines at 20'. Thus, a different local magnetic resonance frame of reference is established by moving the chassis and the static field magnets and related components mounted thereto. The computer records movement of the chassis between positions. Therefore, each new local magnetic resonance frame of reference is in a known position and orientation relative to all of the preceding local magnetic resonance frames of reference. Magnetic resonance information gathered in all of the various frames of reference can be transformed into a single, common working frame of reference. In this manner, the system can display an image of the subject encompassing features in a relatively large region. Because the HIFU unit 16 is mounted on the same chassis as the static field magnet, the frame of reference of the HIFU unit remains fixed with respect to the frame of reference of the static field magnet. Thus, the system can be operated to treat the subject while the chassis is in one position and then moved to a new position to perform additional treatments on tissues at other locations within the subject's body. In effect, the computer constructs a mosaic of the relatively small magnetic resonance images so that the mosaic as a whole encompasses a large region of the subject.

The gradient coils may have shapes other than the shapes discussed above with reference to FIG. 4. For example, the X and Y gradient coils may be circular. Also, where the static field magnet does not inherently provide a field gradient in the axial or Z direction, a further coil or coils may be provided. For example, the Z gradient coil may include a circular solenoid coaxial with the central axis of the static field magnet.

Figure 9:
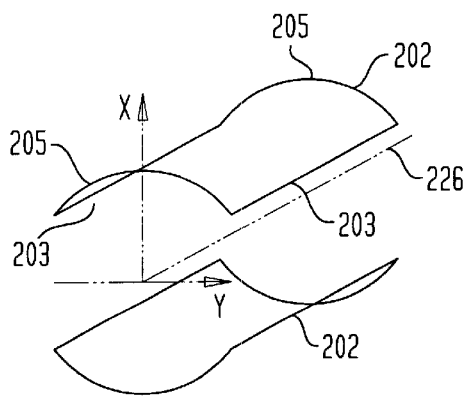
FIG. 9 is a diagrammatic perspective view depicting gradient coils in accordance with a further embodiment of the invention.
Figure 10:
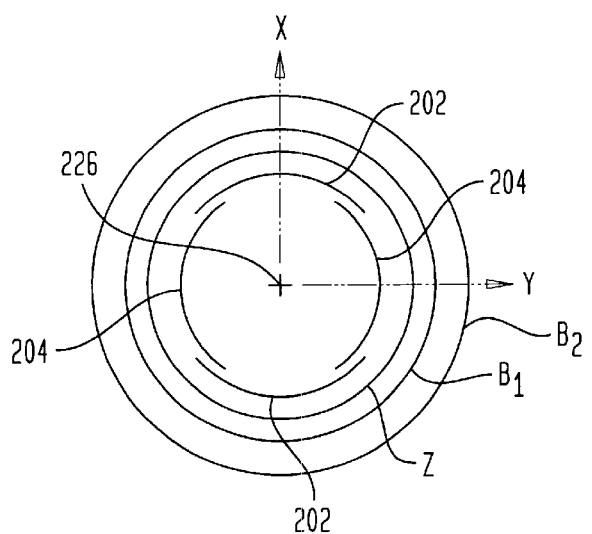
FIG. 10 is a diagrammatic elevational view depicting gradient coils of FIG. 10 in conjunction with other elements of the apparatus.

In a further alternative embodiment, the X-gradient coils may be formed as a pair of opposed saddle-shaped coils 202 (FIGS. 9 and 10) arranged on opposite sides of the central axis 226 of the static field magnet. As best seen in FIG. 10, each X-gradient coil 202 has elongated runs 203 extending generally codirectionally with the central axis, and arcuate runs 205 extending partially around the central axis. The arcuate runs are spaced apart from one another in the direction along the X axis of the magnetic resonance frame of reference. As seen in FIG. 9, the gradient coil assembly may include a similar pair of saddle-shaped coils 204 spaced apart from one another in the Y direction. The arcuate runs of the X and Y gradient coils at the forward ends of the coils are disposed forwardly of the cryostat, whereas the elongated straight runs may extend rearwardly through the central bore of the cryostat. The X and Y gradient coils partially overlap one another as seen in end view along the central axis 226. In a further variant, the elongated runs of the saddle-shaped coils may extend on the outside of the cryostat.

Figure 11:
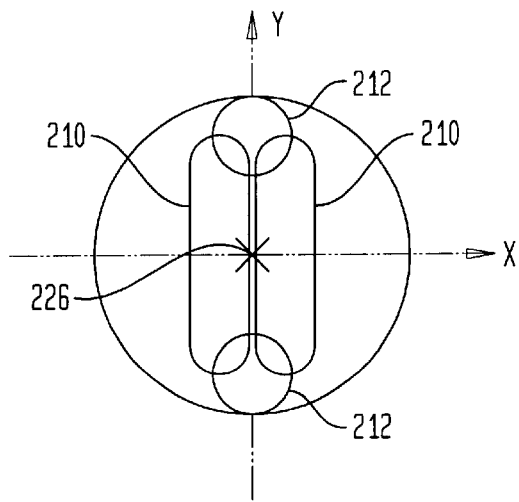
FIG. 11 is a diagrammatic elevational view depicting gradient coils in accordance with yet another embodiment of the invention.

In a further variant the X-direction gradient coils 210 (FIG. 11) are elongated in the Y direction, so that these coils can impose an X direction gradient throughout an elongated imaging region having a relatively large dimension in the Y direction. The Y-direction gradient coils 212 are spaced relatively far apart, so that these coils can also apply the Y direction gradient over the same elongated imaging region. The gradient coils may be of different sizes. For example, the X-direction gradient coils 212 may be of different dimensions.

Figure 12:
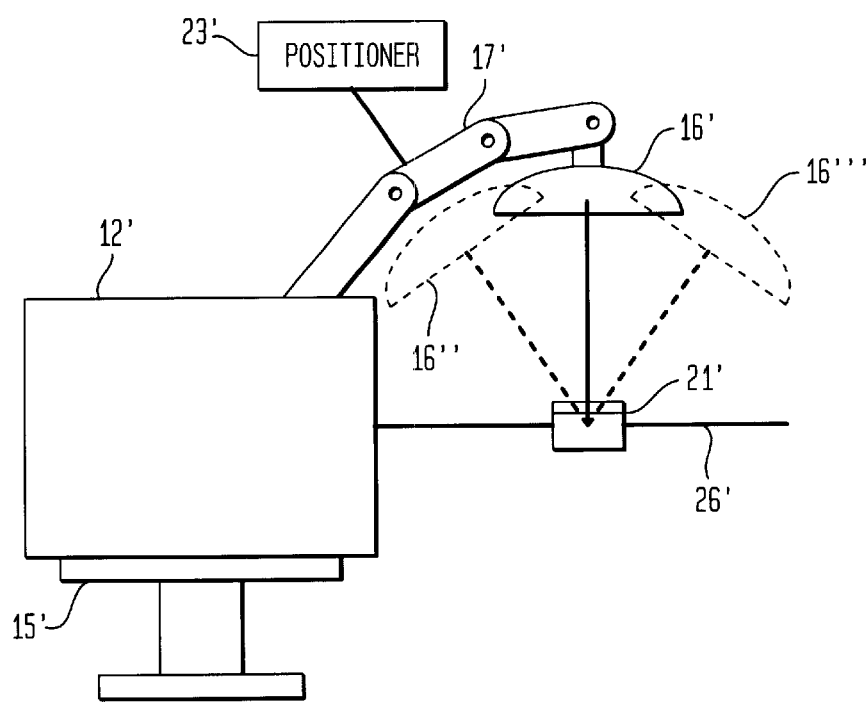
FIG. 12 is a diagrammatic elevational view depicting apparatus in accordance with yet another embodiment of the invention.

In place of the phased array HIFU units discussed above, the HIFU unit may have a fixed focus, and the arm 17 or mounting 19 (FIG. 1) may be may be articulated so that the focus of the ultrasound can be moved by turning the axis 74 of the HIFU unit 16 or moving the HIFU unit relative to the chassis 15. In a further variant, an articulated arm 17' or mounting 19' supporting the HIFU unit 16' (FIG. 12) can be combined with the phased array. The articulated arm 17' has a positioning device 23' associated with is so that the position and orientation of the HIFU unit 16' relative to chassis 15' can be varied. However, the position and orientation of the HIFU unit 16' in the local magnetic frame of reference defined by the static field magnet remain known. This approach allows the operator to direct the ultrasonic energy into the subject's body from various directions, as at positions 16" and 16''', so as to avoid interfering body structures. The control computer can display a marker on the image of the subject which indicates the location of the center of the energy application zone 21', so that the operator can move the energy application zone to the desired position.

In a further variant, the ultrasonic transducers may be mounted on a deformable resilient flange and the flange may be selectively deformed by an actuator to vary the focus of the ultrasonic transducers and thus adjust the focus to the desired location. Alternatively, each transducer can be pivotally mounted on the instrument frame, and the pivotal mountings can be linked to one another so that the transducers pivot towards and away from the axis of the HIFU unit in unison. In a further alternative embodiment the HIFU unit may include ultrasonic transducers disposed in an array coaxial with the central axis of the static field magnet, such as an annular arrangement around the forward side of the magnet assembly. In such an arrangement, the ultrasonic axis is coaxial with of the central axis of the magnet. Here again, the ultrasonic transducers may be mounted on a deformable flange or movable element so that the focus of the ultrasonic energy can be adjusted.

In further variants, the ultrasonic transducers or HIFU unit can be replaced by other devices for applying energy so as to heat tissue at a spot within the body. For example, a system for applying focused radiofrequency (RF) energy can be utilized. The RF system can be mounted on the along with the magnetic resonance components. In a further variant, the focused RF energy may be provided by the same transmitter and antenna used for magnetic resonance operations.

In the arrangements discussed above, the energy applying device moves with the magnet relative to the patient as the positioning system moves the instrument chassis. In an alternative arrangement (FIG. 13) an energy applying device 316 is mounted on one positioning system 318 whereas the magnetic resonance apparatus 312, including the static field magnet, is mounted on a separate positioning system 323. Both of these positioning systems are supported by rails 325 mounted overhead, so that the operator can move the components within the room. In use of this apparatus, the energy applying device is positioned relative to the subject in a separate step from the step of positioning of the magnetic resonance device. Here again, however, the energy applying device is positioned so that it can heat tissues in an energy application zone 321 within the field of view of the magnetic resonance device, and in alignment with the body structure to be treated. The magnetic resonance device may be used to aid this positioning if the heating device is actuated during the positioning stage, so that the spot heated by the heating device can be located in the magnetic resonance image or otherwise detected by the magnetic resonance device. Alternatively, the computer may be arranged to display an indication of the center point of the energy application zone superposed on the image of the subject. The actuation used during the positioning step preferably consists of subthreshold doses which heat the tissue only slightly, and does not permanently damage the tissue.

Preferably, positioning systems 323 and 318 are arranged to track the position and orientation of the magnetic resonance apparatus 312 and energy applicator 316 in a common frame of reference, such as in the frame of reference of rails 325. The steps of positioning of the magnetic resonance apparatus 312 and the energy applicator 316 in alignment with one another, with energy application zone 321 intersecting magnetic resonance volume 320 can be performed partially or entirely with based on data supplied by the positioning systems.

Using known techniques in the position sensing arts, the positioning system or systems may be registered with fiducial markers or anatomical landmarks on the patient, and may be registered with previously-acquired image data, such as MRI or CT data defining a three-dimensional image of the subject. For example, a probe 330 may be connected to a position detector 332 adapted to provide the position of the probe tip in the frame of reference of magnetic resonance device 312 (the local magnetic frame of reference), or in another frame of reference having a known relationship to the local magnetic frame of reference. The previously-acquired image data includes images 332' of identifiable points 332 on the subject's body, which may be naturally-occurring anatomical features such as prominent bony protuberances or fiducial markers attached to the subject before acquisition of the image data. By touching the tip of probe 330 to identifiable points 332, the operator inputs the locations of these points in the local magnetic frame of reference to the control computer. By manipulating a cursor on a monitor displaying the previously-acquired image until the cursor is aligned with the identifiable points, the operator inputs the locations of these points in the frame of reference of the previously-acquired image data. Once the computer has the locations of the same points in both frames of reference, it can derive the transform between the two frames of reference using known techniques.

Once the transform is known, the previously-acquired image data can be used to supplement the data acquired by the magnetic resonance unit 312. For example, during the step of positioning the magnetic resonance and heating devices, representations of the aim points of these devices can be depicted on a display showing the previously acquired image, and these can be moved by moving the devices relative to the patient until the aim points are depicted as aligned on the region to be treated. The same approach can be used to align a single instrument incorporating both MR and heating capabilities.

In a variant of this approach, the movable magnetic resonance device is not used to acquire an image of the subject. Rather, the movable magnetic resonance device is used to acquire magnetic resonance data only in a single voxel at a known location in the local magnetic resonance frame of reference so as to monitor the heating process. Thus, the movable magnetic resonance apparatus may be used to monitor temperature in a single voxel aligned with the focal spot of the energy-applying device, during application of test doses or during application of therapeutic doses. The operations discussed above, such as defining treatment volumes or avoidance zones, may be performed in substantially the same manner; the image displayed to the operator is based on the previously-acquired image data. If the movable magnetic resonance device is not used for imaging, magnet requirements such as field uniformity and gradient linearity can be relaxed considerably, which in turn allows significant reductions in the size and cost of the apparatus. This approach depends upon the subject remaining in fixed position during the treatment. In a variant of this approach, a marker on the subject may be tracked so as to track and compensate for movement of the subject. Such a marker and compensation scheme also may be used where the movable magnetic resonance device is used to acquire images.

In the preferred embodiments discussed above, the magnet of the magnetic resonance apparatus is a single-sided, movable magnet. Other movable magnets can be used. For example, certain movable superconducting magnets have been used for magnetic resonance imaging. These magnets have dual coils mounted to a movable frame, so that the subject is disposed between the coils. Also, aspects of the invention such as the use of test points, treatment volumes and avoidance zones can be practiced even when the procedure is conducted within a conventional fixed magnetic resonance magnet.

In the embodiments discussed above, the focal spot of the HIFU unit or other energy applicator may be made as small as possible so that the treatment can be precisely applied. In a method according to a further embodiment of the invention, the energy applying device is still focused on a relatively small focal spot. However, the focal spot is swept over a larger "pseudo-focal region" (hereinafter "PFR") while applying energy. The PFR typically is of larger size than the focal region. For example, the PFR may have dimensions on the order of 1 cm or so. The sweeping process is performed so as to heat the entire PFR, or a portion of the PFR, to or above the desired temperature. Most preferably, that portion of the PFR which reaches the desired temperature reaches such temperature at about the same time. In the sweeping process, the focal spot moves throughout the PFR either in a repetitive pattern or in a pseudorandom pattern so as to heat different locations in the PFR at successive times. The locations heated at successive times need not be contiguous or even adjacent to one another. Thus, the focal spot may skip from location to location within the PFR, so that the focal spot is located at widely-separated points within the PFR at successive times. For example, the focal spot may be moved in a raster-like pattern 404 throughout a PFR 402a so that neighboring points are heated at successive times.

The average power applied to each point within the PFR may be controlled by controlling the duty cycle at each location. As used in connection with the pseudofocal region, the term "duty cycle" refers to the proportion of the entire heating time for the PFR that the energy is applied to at the particular point. For example, if energy is applied to the PFR by sweeping a focal region throughout the PFR for a period of five minutes, and the focal spot encompasses a particular location for a total of five seconds during that five minute period, then the duty cycle at that spot is $\frac{1}{60}$ or about 1.6%. The duty cycle need not by uniform within the PFR. For example, where a spherical PFR is to be heated to above the threshold temperature uniformly, so that all portions of the PFR reach the threshold temperature at about the same time, the center of the PFR may be treated with a lower duty cycle than the outer portions of the PFR so as to compensate for the more rapid heat loss from the outer portions to the surrounding tissues. For example, the duty cycle at location 406b may be lower than the duty cycle at location 406a. Alternatively or additionally, the average rate of power application to various points within the PFR can be made non-uniform by varying the power applied to the focal spot so that the power level is different for different locations of the focal spot within the PFR. Moreover, the size of the focal spot can be varied, by adjusting the HIFU unit or other energy-applying device, so as to vary the power density (watts/cm$^3$ of tissue within the focal spot) as the focal region moves.

A PFR may have a wide variety of shapes as, for example, spherical, elliptical, rod-like, generally rectangular or the like. Typically the shape of the PFR is selected so that the PFR is a "simply-connected" region. As used herein, the term "simply-connected" refers to a region such that, for any two points within the region, a straight line connecting the two points will be disposed entirely within the region. The aforementioned shapes are simply connected. By contrast, a toroid is not simply-connected.

The energy input throughout the PFR can be calculated by monitoring the temperature at various locations within the PFR as, for example, by magnetic resonance temperature measurements at a point or points within a PFR or, alternatively, by capturing a continuous MRI map or image, which may be visually displayed. Using information obtained during the heating cycle, the heating process can be controlled manually or automatically so as to vary the amount of energy input to various regions of the PFR and terminate the heating process when the desired threshold temperature is reached in all regions of the PFR. The heating process can be terminated selectively in different regions of the PFR as each region reaches the desired temperature. For example, where the desired temperature is a threshold temperature sufficient to kill the tissue, the heating process is terminated as each region of the PFR reaches the threshold temperature. Alternatively or additionally, the heating process can be controlled by prediction using test points in the manner discussed above.

Figure 14:
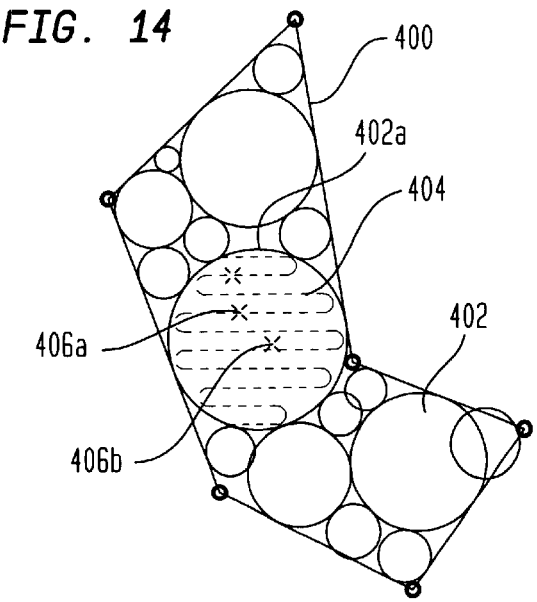
FIG. 14 is a diagram depicting yet another embodiment of the invention.

The position of the PFR can be controlled in substantially the same way as discussed above for control of the focal spot. For example, in a computer controlled system where the computer prevents ablation of an avoidance zone containing sensitive anatomical structures, the computer can be controlled to inhibit energy application to any PFR which overlaps with the avoidance regions. Also, in a system as discussed above with reference to FIG. 7, where the user supplies geometrical coordinates for the volume to be treated, the operator controlling the process, or the computer, may select one or more PFRs having shapes which fit well with the regions to be ablated. For example, as shown in FIG. 14, the operator has defined an a treatment volume 400 encompassing the region of the subject to be treated. The operator can then define a set of PFRs 402 which fill the treatment volume. The operator can enter the boundaries of the PFRs into the computer in the same manner as the operator enters the boundaries of the treatment volume. The computer then actuates the energy applicator to heat each PFR.

As these and other variations and combinations of the features discussed above can be utilized without departing from the present invention, the foregoing description of the preferred embodiments should be taken by way of illustration rather than by way of limitation of the invention as defined by the claims.

What is claimed is:

1. Apparatus for treating a mammalian subject comprising:
   (a) an applicator adapted to receive input energy and apply energy within the body of a subject, said applicator being selectively aimable at different points within the body of the subject, wherein said applicator can be actuated selectively to heat test points in or near a treatment volume within the subject;
   (b) applied energy record means for recording the amount of input energy supplied to the applicator when said applicator is actuated to heat said test points;
   (c) magnetic resonance apparatus for determining a degree of heating of the tissue at each said test point when said applicator is actuated to heat said test points; and
   (d) calculation means for deriving a relationship between input energy supplied by said applicator and degree of heating for treatment locations other than said test points within said treatment volume from the degrees of heating of said test points and the amounts of energy supplied said applicator to said test points.

2. Apparatus as claimed in claim 1 further comprising control means for controlling supply of input energy to said applicator when said applicator is actuated to apply energy at said treatment locations so that the amount of input energy supplied to said actuator during operation to supply energy to each said treatment location is selected at least in part on the basis of the relationship between input energy and heating for such treatment location derived by said calculation means.

3. A method of treating a mammalian subject comprising the steps of:
   (a) selecting a treatment volume within said subject having boundaries defined in a working frame of reference;
   (b) actuating an applicator to apply energy at a plurality of test points in or adjacent the treatment volume;
   (c) determining a degree of heating of the tissue at each said test point;
   (d) deriving a relationship between energy supplied by said applicator and degree of heating for treatment locations other than said test points within said treatment volume from the degrees of heating of said test points and the energy applied by said applicator to said test points; and
   (e) actuating the applicator to apply energy at a plurality of said treatment locations within said treatment volume, the amount of energy applied by said actuator at each said treatment location being selected at least in part on the basis of the relationship between energy and heating for such treatment location derived in said deriving step.

4. A method as claimed in claim 1 wherein said step of determining a degree of heating for each said test point includes the step of acquiring magnetic resonance information for each said test point.

5. A method as claimed in claim 4 further comprising the step of acquiring magnetic resonance information for at least one point in said treatment volume and determining a result of the energy applied in said treatment volume from such magnetic resonance information.

6. A method as claimed in claim 1 wherein said energy applied at said test points is at a level less than a threshold level required to cause permanent change in tissues at said test points.

7. A method as claimed in claim 1 wherein said step of deriving a relationship for treatment locations includes the steps of deriving a relationship between energy supplied by said applicator and degree of heating for each of said test points and interpolating between such relationships over distance between said test points.

8. A method as claimed in claim 1 wherein the boundaries of the treatment zone include one or more polyhedral primitives and wherein said test points are disposed adjacent vertices of said polyhedral primitives.

9. A method as claimed in claim 1 further comprising the step of displaying an image of the subject in said working frame of reference encompassing the region of the subject to be treated and displaying a visual representation of said boundaries superposed on said image.

10. A method as claimed in claim 9 wherein said step of selecting a treatment volume is performed by applying manual inputs to a control element to adjust said boundaries while said visual representation is displayed.

11. A method as claimed in claim 1 wherein said step of actuating the applicator to apply energy at said treatment locations is performed by automatically adjusting the aim of the applicator to different treatment locations according to a preselected sequence and operating the applicator while the applicator is aimed at each such treatment location.

12. A method as claimed in claim 11 wherein said preselected sequence of treatment locations is a raster scan so that said treatment locations are treated in an order corresponding to the spatial arrangement of such locations within said treatment volume.

13. A method as claimed in claim 11 wherein said preselected sequence of treatment locations is pseudorandom pattern.

14. A method as claimed in claim 11 wherein said step of applying energy is applied so as to ablate the tissue at each treatment location.

15. A method as claimed in claim 14 wherein said step of applying energy is performed so as to apply energy to each said treatment location for one second or less.

* * * * *

UNITED STATES PATENT AND TRADEMARK OFFICE
CERTIFICATE OF CORRECTION

PATENT NO. : 6,516,211 B1 Page 1 of 1
DATED : February 4, 2003
INVENTOR(S) : David E. Acker and Mark Wagshul It is certified that error appears in the above-identified patent and that said Letters Patent is hereby corrected as shown below:

Column 26,
Lines 5, 14, 18, 24, 28 and 37, "claim 1" should read -- claim 3 --.

Signed and Sealed this

Fifth Day of August, 2003

JAMES E. ROGAN
*Director of the United States Patent and Trademark Office*